US 9,988,388 B2

(12) United States Patent
Denat et al.

(10) Patent No.: US 9,988,388 B2
(45) Date of Patent: Jun. 5, 2018

(54) SYNTHESIS OF IMIDAZO[1,2-A]PYRAZIN-4-IUM SALTS FOR THE SYNTHESIS OF 1,4,7-TRIAZACYCLONONANE (TACN) AND N- AND/OR C- FUNCTIONALIZED DERIVATIVES THEREOF

(71) Applicants: UNIVERSITE DE BOURGOGNE, Dijon (FR); CENTRE NATIONAL DE LA RECHERCHE SCIENTIFIQUE (CNRS), Paris (FR)

(72) Inventors: Franck Denat, Quetigny (FR); Pauline Desogere, Dijon (FR); Claire Bernhard, Dijon (FR); Yoann Rousselin, Sainte-Marie-sur-Ouche (FR); Frederic Boschetti, Chevigny-Saint-Sauveur (FR)

(73) Assignees: UNIVERSITE DE BOURGOGNE, Dijon (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days. days.

(21) Appl. No.: 15/092,689

(22) Filed: Apr. 7, 2016

(65) Prior Publication Data
US 2016/0222018 A1 Aug. 4, 2016

Related U.S. Application Data

(62) Division of application No. 14/079,530, filed on Nov. 13, 2013.

(30) Foreign Application Priority Data

Nov. 21, 2012 (FR) .................................... 12 601091

(51) Int. Cl.
| C07D 487/04 | (2006.01) |
| C07D 255/02 | (2006.01) |
| C07D 401/14 | (2006.01) |
| C07F 9/6515 | (2006.01) |
| C07D 401/06 | (2006.01) |
| C07D 301/02 | (2006.01) |
| A61K 49/00 | (2006.01) |
| A61K 49/10 | (2006.01) |
| A61K 51/04 | (2006.01) |
| B01J 31/18 | (2006.01) |

(52) U.S. Cl.
CPC ........ *C07D 487/04* (2013.01); *A61K 49/0002* (2013.01); *A61K 49/0021* (2013.01); *A61K 49/0052* (2013.01); *A61K 49/106* (2013.01); *A61K 51/0482* (2013.01); *B01J 31/182* (2013.01); *C07D 255/02* (2013.01); *C07D 301/02* (2013.01); *C07D 401/06* (2013.01); *C07D 401/14* (2013.01); *C07F 9/6515* (2013.01); *B01J 2231/72* (2013.01)

(58) Field of Classification Search
CPC .................................................... C07D 487/04
See application file for complete search history.

(56) References Cited

U.S. PATENT DOCUMENTS

| 2008/0267882 A1 | 10/2008 | Chen et al. |
| 2011/0070157 A1 | 3/2011 | Zavarzin et al. |
| 2012/0064003 A1 | 3/2012 | Guerbet |

FOREIGN PATENT DOCUMENTS

| EP | 0404605 | 12/1990 |
| FR | 2862217 | 5/2005 |
| WO | 0164826 | 9/2001 |
| WO | 03059397 | 7/2003 |
| WO | 2004054622 | 7/2004 |
| WO | 2005049870 | 6/2005 |

(Continued)

OTHER PUBLICATIONS

Sibbons et al., "The application of manganese complexes of ligands derived from 1,4,7-triazacyclononane in oxidative catalysis", Dalton Trans., vol. 5, Feb. 2006, pp. 645-661.

(Continued)

*Primary Examiner* — Noble E Jarrell
*Assistant Examiner* — John S Kenyon
(74) *Attorney, Agent, or Firm* — Young & Thompson

(57) ABSTRACT

A compound with formula (V')

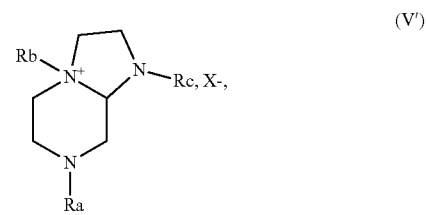

the synthesis method for compound (V'), and its use for the preparation of 1,4,7-triazacyclononane (tacn) and N- and/or C-functionalized derivatives thereof, particularly compounds with formula (I)

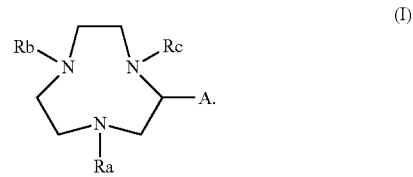

Also, metallic complexes comprising a ligand with formula (I) and a metal and their use for imaging.

6 Claims, No Drawings

(56) References Cited

FOREIGN PATENT DOCUMENTS

WO  2009079024  6/2009
WO  2010108125  9/2010

OTHER PUBLICATIONS

Argouarch et al., "The synthesis of chiral annulet 1,4,7-triazacyclononanes", Tetrahedron Lett., vol. 43, 2002, pp. 3795-3798.
Argouarch et al., "Bifurcated, modular syntheses of chiral annulet triazacyclononanes", Org. Biomol. Chem., vol. 1, Nov. 2003, pp. 4408-4417.
Stones et al., "The synthesis of an isopropyl substituted 1,4,7-triazacyclononane via an in situ sequential macrocyclisation method", Org. Biomol. Chem. vol. 1, May 2003, pp. 2357-2363.
Scheuermann et al., "The synthesis of unsymmetrically N-substituted chiral 1,4,7-triazacyclononanes", Org. Biomol. Chem., vol. 2, Aug. 2004, pp. 2664-2670.
McMurry et al., "Synthesis of 2-(p-Thiocyanatobenzyl)-1,4,7-triazacyclononane-1,4,7-triacetic Acid: Application of the 4-Methoxy-2,3,6-trimethylbenzenesulfonamide Protecting Group in the Synthesis of Macrocyclic Polyamines", Bioconjugate, vol. 4, N°3, 1993, pp. 236-245.
Koek et al., "Direct ring functionalisation of 1,4,7-trimethyl-1,4,7-triazacyclononane and its application in the preparation of functional [L2Mn2O3]-type complexes", Tetrahedron Lett., vol. 47, Apr. 2006, pp. 3673-3675.
Cox et al., "Synthesis of C- and N-Fuctionalised Derivatives of 1,4,7-triyltriacetic acid (NOTA), 1,4,7,10-Tetra-azacyclododecane-1,4,7,10-tetrayltetra-acetic Acid (DOTA), and Diethylenenetriaminepenta-acetic Acid (DTPA): Bifunctional Complexing Agents for the Derivatisation of Antibodies", J. Chem. Soc., Perkin Trans., 1990, pp. 2567-2576.
Singh et al., "Multivalent Bifunctional Chelator Scaffolds for Gallium-68 Based Positron Emission Tomography Imaging Probe Design: Signal Amplification via Multivalency", Bioconjugate Chem., vol. 22, Jul. 2011, pp. 1650-1662.
Riss et al., "NODAPA-OH and NODAPA-(NCS)n: Synthesis, 68Ga-radiolabelling and in vitro characterisation of novel versatile bifunctional chelators for molecular imaging", Bioorg. Med. Chem. Lett., vol. 18, Sep. 2008, pp. 5364-5367.
Simecek et al., "Complexation of Metal Ions with TRAP (1,4,7-Triazacycloneonane Phosphinic Acid) Ligands and 1,4,7-Triazacyclononane-1,4,7-triacetic Acid: Phosphinate-Containing Ligands as Unique Chelators for Trivalent Gallium", Inorg. Chem., vol. 51, 2012, pp. 577-590.
Notni et al., "A Triazacyclononane-Based Bifunctional Phosphinate Ligand for the Preparation of Multimeric 68Ga Tracers for Positron Emission Tomography", Chem. Eur. J., vol. 16, 2010, pp. 7174-7185.
Jeong et al., "Preparation of a Promising Angiogenesis PET Imaging Agent: 68Ga-Labeled c(RGDyK)-Isothiocyanatobenzyl-1,4,7-Triazacyclononane-1,4,7-Triacetic Acid and Feasibility Studies in Mice", J. Nucl. Med., vol. 49, N°5, May 2008, pp. 830-836.
Kim et al., "Synthesis and characterization of a 68Ga-labeled N-(2-diethylaminoethyl)benzamide derivative as potential PET probe for malignant melanoma", Bioorg. Med. Chem., vol. 20, N°16, Jul. 2012, pp. 4915-4920.
Forster et al., "Maleimido-Functionalized NOTA Derivatives as Bifunctional Chelators for Site-Specific Radiolabeling", Molecules, vol. 16, N°6, Jun. 2011, pp. 5228-5240.
Dissoki et al., "Labeling approaches for the GE11 peptide, an epidermal growth factor receptor biomarker", J. Label. Compd. Radiopharm., vol. 54, N°11, Jun. 2011, pp. 693-701.
Hoigebazar et al., "Synthesis and Characterization of Nitroimidazole Derivatives for 68Ga-Labeling and Testing in Tumor Xenografted Mice", J. Med. Chem., vol. 53, N°17, Sep. 2010, pp. 6378-6385.
Kim et al., "Effects of Targeting Moiety, Linker, Bifunctional Chelator, and Molecular Change on Biological Properties of 64Cu-Labeled Triphenylphosphonium Cations", J. Med. Chem., vol. 51, N°10, May 2008, pp. 2971-2984.
Craig et al., "Towards Tumour Imaging with Indium-111 Labelled Macrocycle-Antibody Conjugates", J. Chem. Soc., Chem. Commun., vol. 12, 1989, pp. 794-796.
Koek et al., "Synthesis and properties of hydrophobic [Mn2IV(μ-O)3(L)2]2+ complexes, derived from alkyl substituted 1,4,7-triazacyclonane ligands", Inorg. Chim. Acta, vol. 295, N°2, Jul. 1999, pp. 189-199.
Billington et al., "The synthesis of novel bifunctional linker molecules", Tetrahedron. vol. 47, N°28, Feb. 1991, pp. 5231-5236.
Richman et al., "Nitrogen Analogs of Crowns Ethers", J. Am. Chem. Soc., vol. 96, N°7, 1974, pp. 2268-2270.
Morphy et al., "Towards Tumor Targeting with Copper-Radiolabelled Macrocycle-Antibody Conjugates", J. Chem. Soc. Chem. Commun. vol. 12, 1989, pp. 792-794.

SYNTHESIS OF IMIDAZO[1,2-A]PYRAZIN-4-IUM SALTS FOR THE SYNTHESIS OF 1,4,7-TRIAZACYCLONONANE (TACN) AND N- AND/OR C- FUNCTIONALIZED DERIVATIVES THEREOF

FIELD OF INVENTION

This invention relates to a new synthesis method for the 1,4,7 triazacyclononane (tacn) precursor and its N- and/or C-functionalized derivatives. The method according to the invention comprises the preparation of imadazo[1,2-a]pyrazin4-ium salts that can be used for synthesis of tacn and its N- and/or C-functionalized derivatives. Another purpose of the invention is new N- and/or C-functionalized macrocyclic molecules derived from tacn and the imadazo[1,2-a]pyrazin-4-ium salts.

BACKGROUND OF INVENTION

Polyazamacrocycles and their derivatives are nitrogen-containing macrocycles known for their sequestration properties of transition metals and heavy metals. They have applications in a wide variety of fields including treatment of liquids, catalysis or health and more particularly medical imaging.

Among these macrocyclic systems, derivatives of the tridentate 1,4,7 triazacyclononane (tacn) ligand, macrocycle carrying three nitrogen atoms, possess very good complexing properties, making them likely to be useful for many applications. In particular, the capacity of nitrogen-containing derivatives of tacn to stabilise metal ions with a high oxidation state and particularly Manganese ions (Mn (IV)) explains their use in many catalytic processes, as in olefin polymerisation reactions or olefin epoxidation reactions with hydrogen peroxide in water (Sibbons et al., *Dalton Trans.* 2006, 645-661). In this context, the trimethyl-tacn (metacn) system has been especially studied for its catalytic activity in the form of dinuclear complexes of manganese. Complexes of tacn-Mn(IV) have also been suggested as bleaching agents, particularly in detergents, to replace some oxidants (WO01/64826). Tacn derivatives have also been disclosed as cosmetic agents for hair perm, or as keratin extracting agents (FR2 862 217, WO2005/049870).

The interest in tacn derivatives has been continuously growing during the last approximately ten years, particularly due to the advantages of this type of system for sequestration of radiometals for applications in SPECT (Single Photon Emission Computed Tomography) and PET (Positron Emission Tomography) nuclear imaging. These macrocyclic molecules are then used as a bifunctional chelating agent capable firstly of sequestering the radioactive source (In, Ga, Cu, Y, etc.) and also of coupling with a vector biomolecule. This indirect labeling method is now a preferred method for medical imaging and for radioimmunotherapy.

NOTA is one tacn derivative frequently used in imaging, and corresponds to the tacn possessing three methylcarboxylate functions on nitrogen atoms. Different physicochemical and structural studies have been done on NOTA complexes intended for SPECT/PET imaging or therapy and in particular have demonstrated that the $^{64}$Cu-NOTA and $^{67/68}$Ga-NOTA metallic complexes have good in vivo stability. The radiolabeling rate is also relatively fast, requiring mild radiometallation conditions compatible with labeling of antibody type biological molecules (see for example US2012/064003, WO2009/079024, US2011/0070157).

In order to improve existing systems, efforts have been concentrated on optimization of their properties, particularly by developing C-functionalized macrocycles. C-functionalization is an approach that consists of introducing a "grafting" function onto the carbon skeleton of the macrocycle. The C-functionalization of tacn may optionally be accompanied by the addition of chelating arms on the three nitrogen atoms of the cycle. This approach has been applied for the synthesis of new bifunctional chelating agents. However it is relatively limited, because of the difficulty to synthesize C-functionalized macrocycles.

Access to such "bifunctional chelating" systems requires firstly an efficient method of synthesizing the "basic" macrocycle, in this case the tacn motif, and secondly the ability to selectively functionalize this motif at the nitrogen atoms (N-functionalization) and/or in the carbon skeleton (C-functionalization).

To the knowledge of the Applicant, at the present time only one synthesis method is used for the synthesis of 1,4,7-triazacyclononane (tacn) and its N-functionalized analogues, known under the term "Richman-Atkins cyclization" (Richmans, J. E., Atkins, T. J. *J. Am. Chem. Soc.* 1974, 96, 2268-2270). The method for synthesising tacn described by Richman and Atkins is summarised in the scheme 1 below:

Scheme 1. Richman-Atkins cyclization

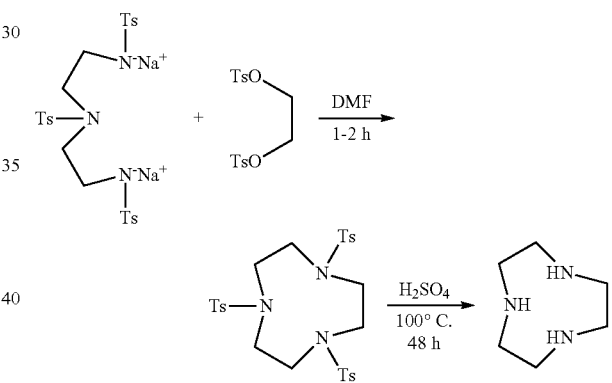

This synthesis method has many disadvantages, particularly the use of tosyl groups during the cyclization step, long reaction times and a global yield of not more than 12%. Drastic conditions for the elimination of tosyl groups ($H_2SO_4$, 100° C. for 2 days) form a major obstacle for transposing this method to a large scale, without considering the problem that this synthesis method is not atom-economic.

"Richman-Atkins" cyclization conditions were used for the preparation of C-functionalized derivatives starting from diols or linear amines functionalized on one of the carbon atoms (Argouarch et al., *Tetrahedron Lett.* 2002, 43, 3795-3798; Argouarch et al., *Org. Biomol. Chem.* 2003, 1, 2357-2363; Stones et al., *Org. Biomol. Chem.* 2003, 1, 4408-4417; Scheuermann et al., *Org. Biomol. Chem.* 2004, 2, 2664-2670; Mc Murry et al., *Bioconjugate Chem.*, 1993, 4, 236-245).

Since the function cannot be introduced into the carbon skeleton by simple C—C coupling, these syntheses make use of biselectrophilic synthons possessing the desired function. This synthesis method is directly inspired from Richman and Atkins' method of obtaining tacn and requires drastic deprotection conditions that considerably limit the nature of functional groups that may be introduced into the macrocycle.

A synthesis method providing access to C-functionalized derivatives was recently described by J. M. Kohlen's team (Koek J. and Kohlen E., *Tetrahedron Lett.* 2006, 47, 3673-3675). In this method, N-methylated tacn (metacn) is oxidized by N-bromosuccinimide (NBS) to lead to the corresponding bicyclic iminium. The addition of potassium cyanide allows the opening of the bicyclic structure and the formation of a nine-member ring. Reduction of the nitrile group can form an amine function allowing the possibility of further functionalization.

Scheme 2. C-functionalization of Kohlen et al.

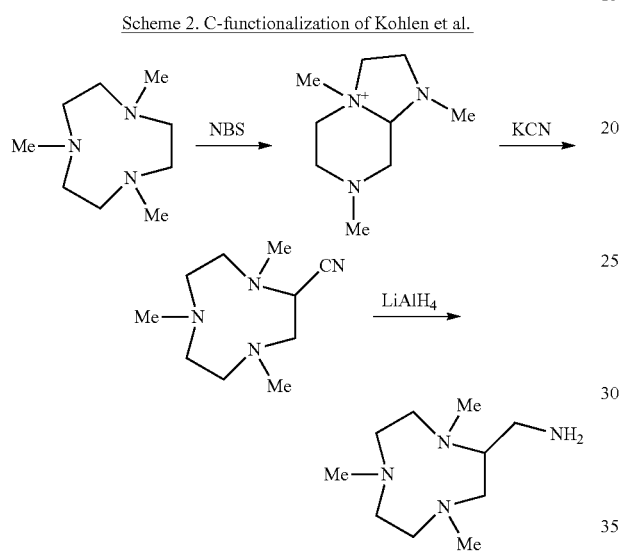

However, this synthesis method requires the preliminary synthesis of metacn by Richman-Atkins cyclization. This method is also very limited because it only provides access to C-functionalized derivatives of metacn. Indeed, methyl groups cannot be removed and therefore, this approach cannot be used for preparation of tacn derivatives possessing coordinating groups on nitrogen atoms (carboxylates, phosphonates, etc.) useful for applications in medical imaging.

Thus, despite the strong potential of C-functionalized tacn systems, very few molecules of this type have been described so far, mainly due to difficulties with synthesis.

Therefore, this invention discloses a new method of synthesis of the 1,4,7-triazacyclononane precursor (tacn) and its N- and/or C-functionalized derivatives. The method according to the invention comprises the synthesis of imidazo[1,2-a]pyrazin-4-ium salts. Another purpose of the invention is new macrocyclic molecules derived from tacn and imidazo[1,2-a]pyrazin-4-ium salts.

DEFINITIONS

In this invention, the following definitions of terms are applicable:
"aliphatic group" applies to any carbonated, acyclic or cyclic, saturated or unsaturated, branched or unbranched group, optionally substituted, excluding aromatic compounds. According to the invention, an aliphatic group preferably comprises 1 to 12 carbon atoms, preferably 1 to 6 carbon atoms. According to one preferred embodiment of the invention, branched or unbranched aliphatic groups are selected from alkyl, cycloalkyl, alkenyl, cycloalkenyl, alkynyl groups;

"alkyl" applies to any saturated linear or branched hydrocarbon chain, optionally substituted, comprising 1 to 12 carbon atoms, and preferably 1 to 6 carbon atoms; more preferably methyl, ethyl, propyl, isopropyl, n-butyl, sec-butyl, isobutyl, tert-butyl;

"cycloalkyl" applies to a cyclic or polycyclic, optionally branched, substituted or unsubstituted alkyl group; preferably a cyclopropyl, cyclopentyl or cyclohexyl group;

"alkenyl" applies to any linear or branched, optionally substituted hydrocarbon chain, carrying at least one double bond and comprising 2 to 12 carbon atoms, and preferably 2 to 6 carbon atoms;

"cycloalkenyl" applies to a cyclic or polycyclic alkenyl group, optionally branched, substituted or unsubstituted; preferably a cyclopropenyl, cyclopentenyl or cyclohexenyl group;

"alkynyl" applies to any linear or branched, optionally substituted hydrocarbon chain carrying at least one triple bond and comprising 2 to 12 carbon atoms, and preferably 2 to 6 carbon atoms;

"alkoxy" applies to an O-alkyl group. One preferred alkoxy group for this invention is the methoxy group;

"aromatic group" applies to a mono- or polycyclic system with 5 to 20, and preferably 6 to 12, carbon atoms possessing one or several aromatic rings (when there are two rings, the term used is a biaryl) among which are included the phenyl group, the biphenyl group, the 1-naphthyl group, the 2-naphthyl group, the anthracenyl group, the pyrenyl group, the tetrahydronaphthyl group, the indanyl group and the binaphthyl group. The term aromatic group also applies to any aromatic ring comprising at least one heteroatom selected from an oxygen, nitrogen or sulphur atom, among which are included quinoline, terpyridinyl, bipyridinyl, guanine, phenantroline, hydroxyquinoline. The aromatic group may be substituted by 1 to 3 substituents selected independently of each other from a group comprising a hydroxyl group, a linear or branched alkyl group comprising 1, 2, 3, 4, 5 or 6 carbon atoms, particularly methyl, ethyl, propyl, butyl, an alkoxy group or a halogen atom, particularly bromine, chlorine and iodine. When the aromatic group is substituted, it may be meta and/or para and/or ortho substituted; and if the aromatic group is a benzyl, it may further be meso-substituted.

"halo" refers to a fluoro, chloro, bromo, or iodo. Bromo and iodo are the preferred halo groups.

"heteroatom" refers to nitrogen, oxygen, sulphur or phosphorus atoms;

"amino" refers to a —$NH_2$ group or any group derived from —$NH_2$ by substitution of one or several hydrogen atoms by an aliphatic or aromatic, substituted or unsubstituted organic group, wherein when the aliphatic or aromatic group is substituted, it is by one or several substituents, selected from the group comprising halo, hydroxyl, oxo, nitro, amido, carboxy, amino, cyano, haloalkoxy, haloalkyl. —$NH_2$ derivative groups are preferably alkylamino groups, in other words N-alkyl groups including the monoalkylamino and dialkylamino groups. In one embodiment of the invention, by amino, it is not referred in the present invention to thiourea derivatives.

"function that can lead to click chemistry reactions" applies to chemical functions such as azide, alkyne, norbornene, cyclooctene, or 1,2,4,5 tetrazine. These functions are well known to those skilled in the art as being useful in click chemistry reactions. This type of reaction has been described particularly by Sharpless (Angewandte Chemie International Edition 40 (11): 2004-2021). One click chemistry reaction currently used is the Huisgens cycloaddition reaction between an azide and an alkyne.

"macrocyclic moiety" refers to molecule containing a ring of nine or more atoms with three or more donor atoms that can coordinate a metal, particularly a cation. The macrocyclic moiety may be polyazamacrocyclic compounds, such as for example tacn, cyclen, cyclam, 13aneN4 derivatives.

"bismacrocyclic" refers to a molecule containing two "macrocyclic moieties" as described above, linked together through an aliphatic or aromatic spacer, such as for example a biscyclam derivative (AMD3100 derivative).

"organometallic moiety" refers to a molecule containing a transition metal of potential therapeutic interest (Ru, Au, Rh, Pt, . . . ) coordinated to an organic ligand through a carbon-metal coordination bond, such as for example a Ru (arene) complex (RAPTA Ru-arene, Ru(arene)-en).

When groups may be substituted, they may be substituted by one or several substituents, preferably one, two or three substituents. Substituents may for example be selected from the group comprising halo, hydroxyl, oxo, nitro, amido, carboxy, amino, cyano, haloalkoxy, haloalkyl.

DETAILED DESCRIPTION

Synthesis Method

This invention applies to a method for the synthesis of triazacyclononane (tacn) and derivatives of N- and/or C-functionalized tacn, these compounds corresponding to the general formula (I")

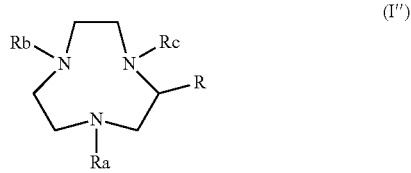

and its salts wherein
Ra, Rb and Rc may be identical or different and each represents
  a hydrogen atom, or
  a —(CH$_2$)$_n$—R' group wherein n is equal to 0, 1, 2, 3, 4, 5 or 6, n is preferably equal to 0, 1, 2 or 3, and R' represents
    a saturated or unsaturated, branched or unbranched, substituted or unsubstituted aliphatic group, comprising 1 to 12 carbon atoms, preferably when the aliphatic group is substituted, it is by one or several substituents, selected from the group comprising halo, hydroxyl, oxo, nitro, amido, carboxy, amino, cyano, haloalkoxy, haloalkyl;
    when n is equal to 0, R' represents —CH(COOR'$_4$)(CH$_2$)$_{m4}$COOR'$_5$ wherein m$_4$ is equal to 1, 2 or 3 and R'$_4$, R'$_5$ are identical or different and each represent a hydrogen atom or a group selected from alkyl, benzyl, paranitrobenzyl, pentafluorobenzyl, N-hydrosuccinimide (NHS), sulfo-NHS group; preferably m$_4$ is equal to 2, R'$_4$ represents tBu and R'$_5$ represents H;
    an unsubstituted benzyl group or a benzyl group substituted in the meso and/or meta and/or para and/or ortho position by one or several radicals selected from cyano, nitro, amino, halo, alkoxy, hydroxy radicals;
    an unsubstituted methyl pyridine group or a methyl pyridine group substituted by one or several groups selected from cyano, nitro, amino, halo, alkoxy, hydroxy groups;
    an aromatic group, preferably selected from the group comprising phenyl, biphenyl, 1-naphthyl, the 2-naphthyl, anthracenyl, pyrenyl, tetrahydronaphthyl, indanyl, binaphthyl, terpyridinyl, bipyridinyl, guanine phenantroline, hydroxyquinoline and quinoline group, more preferably a quinoline group;
    a SH group;
    a —C(=O)—OR'$_1$ group wherein R'$_1$ represents a hydrogen atom or a saturated or unsaturated, branched or unbranched, substituted or unsubstituted aliphatic group, comprising 1 to 12 carbon atoms, wherein when the aliphatic group is substituted, it is by one or several substituents, selected from the group comprising halo, hydroxyl, oxo, nitro, amido, carboxy, amino, cyano, haloalkoxy, haloalkyl, aryl, and preferably R'$_1$ represents a hydrogen atom or a methyl, ethyl, tert-butyl, benzyl, paranitrobenzyl, pentafluorobenzyl, N-hydrosuccinimide (NHS), sulfo-NHS group;
    a —(CH$_2$)$_2$—OR'$_1$ group wherein R'$_1$ is as defined above;
    a —C(=O)—NHR'$_1$ group wherein R'$_1$ is as defined above;
    a —C(=O)—SR'$_1$ group wherein R'$_1$ is as defined above; preferably R'$_1$ represents a benzyl, methyl or phenyl;
    a —P(=O)—R'$_2$R'$_3$ group wherein R'$_2$ and R'$_3$ may be identical or different and each represents a —(CH$_2$)$_{m1}$—R"$_1$ group wherein m$_1$ is equal to 0, 1, 2, 3, 4, 5 or 6, preferably equal to 0, 1, 2 or 3 and R"$_1$ represents a saturated or unsaturated aliphatic chain, possibly interrupted by one or several oxygen, nitrogen or sulphur atoms; preferably R"$_1$ represents a —(CH$_2$)$_{m2}$—OR'$_1$ group wherein m$_2$ is equal to 0, 1, 2, 3, 4, 5 or 6, preferably equal to 0, 1, 2 or 3 and R'$_1$ is as defined above, preferably ethoxy, OH;
    a —(CH$_2$)$_{m3}$—(C=O)—OR'$_1$ group wherein m$_3$ is equal to 1, 2, 3 or 4 and R'$_1$ is as defined above;
    an alkyl group comprising 1 to 12 carbon atoms, preferably a methyl;
R represents a hydrogen atom or a group A;
A represents
  a —(CH$_2$)$_{w1}$-A' group wherein w$_1$ is equal to 0, 1, 2, 3 or 4, preferably w$_1$ is equal to 0 or 1, and A' represents
    a saturated or unsaturated, branched or unbranched, substituted or unsubstituted aliphatic group comprising 1 to 12 carbon atoms, preferably when the aliphatic group is substituted, it is by one or several substituents, selected from the group comprising halo, hydroxyl, oxo, nitro, amido, carboxy, amino, cyano, haloalkoxy, haloalkyl;
    a cyano group; A' preferably represents a cyano group when w$_1$ is equal to 0;

an aliphatic or aromatic group containing a function that can lead to click chemistry reactions, and more particularly a group containing an azide, alkyne, cyclooctene or 1,2,4,5 tetrazine function;

an unsubstituted benzyl group or a benzyl group substituted in the meso and/or meta and/or para and/or ortho position by one or several groups selected from cyano, nitro, amino, halo, alkoxy, hydroxy groups;

an unsubstituted methyl pyridine group or a methyl pyridine group substituted by one or several groups selected from cyano, nitro, amino, halo, alkoxy, hydroxy groups;

an aromatic group, preferably selected from the group comprising phenyl, biphenyl, 1-naphthyl, the 2-naphthyl, anthracenyl, pyrenyl, tetrahydronaphthyl, indanyl, binaphthyl, terpyridinyl, bipyridinyl, guanine, phenantroline, hydroxyquinoline and quinoline group;

a $(CH_2)_{w2}$—NA"A'" group wherein $w_2$ is equal to 0, 1, 2, 3 or 4, and preferably $w_2$ is equal to 1, and wherein A" and A'" are identical or different and each represents a hydrogen atom;

a saturated or unsaturated, branched or unbranched, substituted or unsubstituted aliphatic group, comprising 1 to 12 carbon atoms, preferably when the aliphatic group is substituted, it is by one or several substituents, selected from the group comprising halo, hydroxyl, oxo, nitro, amido, carboxy, amino, cyano, haloalkoxy, haloalkyl;

a —$(CH_2)_{w3}$-A"$_1$ group wherein $w_3$ is equal to 0, 1, 2, 3, 4, 5 or 6, preferably equal to 0, 1, 2 or 3 and A"$_1$ represents a saturated or unsaturated, branched or unbranched, substituted or unsubstituted aliphatic chain that can contain 1 to 4 (C=O) or (C=S) or (P=O) motifs and/or one or several heteroatoms, one or several substituted aromatic meta and/or para and/or ortho groups; preferably A"$_1$ represents a —$(CH_2)_{w4}$—C(=O)-A'"$_1$ group wherein $w_4$ is equal to 0, 1, 2, 3, 4, 5 or 6, and $w_4$ is preferably equal to 0 or 1, and A'"$_1$ represents an —OY group wherein Y represents a hydrogen, a branched or unbranched alkyl group, a substituted or unsubstituted benzyl group or a succinimide derivative, preferably Y represents a hydrogen, or a methyl, ethyl, tert-butyl, benzyl, paranitrobenzyl, pentafluorobenzyl, N-hydrosuccinimide (NHS), sulfo-NHS group;

a saturated or unsaturated, branched or unbranched aliphatic group comprising 1 to 12 carbon atoms, preferably a methyl group;

a benzyl group substituted in the para position by a group selected from cyano, nitro, isothiocyanate, amino, alkoxy groups;

preferably, the —$(CH_2)_{w3}$-A"$_1$ group is a —$CH_2$—C(=O)—OH, —$CH_2$—C(=O)—OtBu, —$CH_2$—P(=O)-(Me)OCH$_2$CH$_2$COOH, —CH$_2$PhOCH$_2$C≡CH, C(=O)CH$_2$CH$_2$COOH, —C(=O)—CH$_2$PhNO$_2$, —C(=O)—CH$_2$PhNH$_2$ or —C(=O)CH$_2$PhNCS group;

a —C(=O)—Z group wherein Z represents an organic fluorescent motif, for example such as fluorescein, rhodamine, polymethine, boron dipyrromethene, porphyrine, phthalocyanine, squaraine or a derivative of these groups;

a —C(=O)—Z' group wherein Z' contains a macrocyclic or bismacrocyclic moiety;

a —C(=O)—Z" group wherein Z" contains an organometallic moiety;

A" and A'" form together an anhydride ring such that $(CH_2)_{w2}$—NA"A'" is of formula:

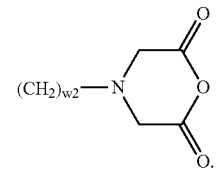

When A represents a $(CH_2)_{w2}$—NA"A'" wherein at least either A" or A'" represents a —C(=O)—Z group wherein Z represents an organic fluorescent motif, the fluorescent motif is preferably coupled with the macrocyclic unit by peptidic coupling, possibly but not necessarily through an amino acid spacer. According to one preferred embodiment, the fluorescent motif is more particularly a boron dipyrromethene type motif (Bodipy®) preferably comprising a COOH or NH$_2$ type binding functional group.

C-functionalized tacn derivatives and C- and N-functionalized tacn derivatives are more specifically represented by the general formula (I); while tacn and its N-functionalized derivatives are represented more specifically by the general formula (I'):

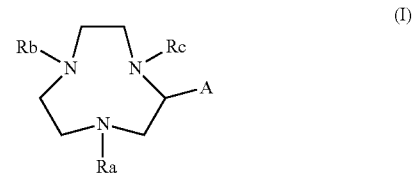

(I)

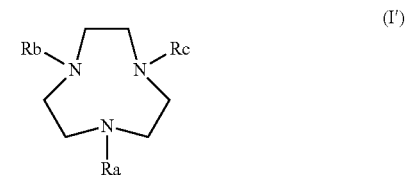

(I')

and their salts, wherein Ra, Rb, Rc and A are as defined in the general formula (I").

Formula (I) corresponds to the general formula (I") wherein R is an A group.

Formula (I') corresponds to the general formula (I") wherein R is a hydrogen atom.

The method for preparation of compounds with formula (I") includes the steps shown in scheme 3:

Scheme 3. Synthesis method for compounds with formula (I")

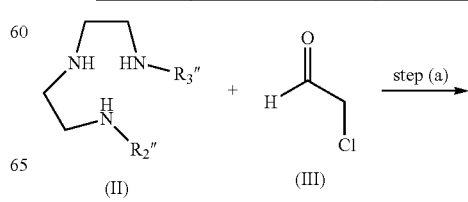

-continued

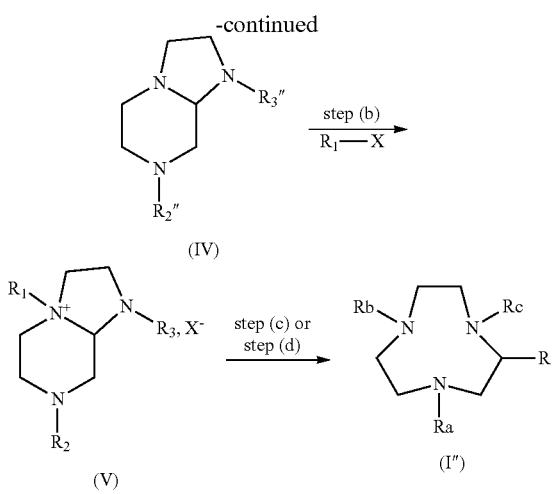

In particular, steps (c) and (d) leading from compound (V) to compound (I″) are as follows (Scheme 4), the steps shown in dashed lines being optional:

Scheme 4. Steps (c) and (d) in the synthesis method for compounds with formula (I″)

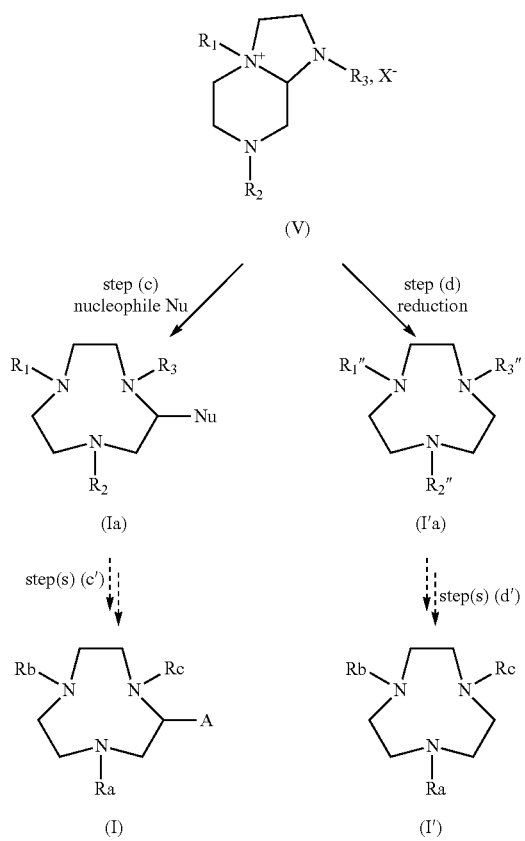

Compounds (Ia) and (I′a) are special cases of formulas (I) and (I′) respectively, that themselves form special cases of the general formula (I″) as mentioned above.

Steps (c), (c′), (d) and (d′) make use of chemical modifications known to those skilled in the art. The essential point is that there is an efficient and versatile method of preparing the compound with formula (V).

Consequently, this invention relates to a method for preparation of a compound with formula (V)

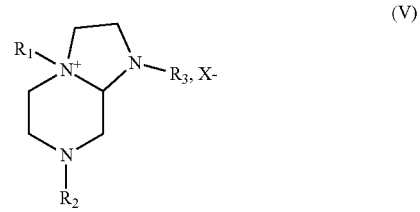

wherein
X represents a radical selected from bromo, iodo or chloro radicals;
$R_1$ represents a $(CH_2)_p$—B radical wherein
p is equal to 1, 2, 3 or 4;
B represents
a hydrogen atom;
an unsubstituted phenyl radical or a phenyl radical substituted in the meta and/or para and/or ortho position by one or several radicals selected from cyano, nitro, amino, halo, (preferably bromo or iodo), alkoxy (preferably methoxy), hydroxy radicals;
an unsubstituted pyridine radical or a pyridine radical substituted by one or several radicals selected from cyano, nitro, amino, halo (preferably bromo or iodo), alkoxy (preferably methoxy), hydroxy radicals;
$R_2$ represents $R_1$, $R_2″$, $R_2″$ modified by reaction with $R_1$—X or a Boc group,
where $R_2″$ represents a hydrogen atom or an aliphatic or aromatic group, optionally substituted by one or several radicals selected from cyano, nitro, amino, halo, alkoxy, hydroxy radicals, and preferably $R_2″$ represents H or —$(CH_2)_2NH_2$;
preferably $R_2$ represents $R_1$ or $(CH_2)_2N(R_1)_2$;
$R_3$ represents $R_1$, $R_3″$, $R_3″$ modified by reaction with $R_1$—X or a Boc group,
where $R_3″$ represents a hydrogen atom or an aliphatic or aromatic group, optionally substituted by one or several radicals selected from cyano, nitro, amino, halo, alkoxy, hydroxy radicals, and preferably $R_3″$ represents H or —$(CH_2)_2NH_2$;
preferably $R_3$ represents $R_1$ or $(CH_2)_2N(R_1)_2$;
and preferably, $\{R_2, R_3\}$ represents $\{R_1, R_1\}$, $\{R_1, (CH_2)_2N(R_1)_2\}$, $\{(CH_2)_2N(R_1)_2, R_1\}$ or $\{Boc, Boc\}$;
comprising the following successive reaction steps (a) and (b):
a step (a) during which the compound with formula (II)

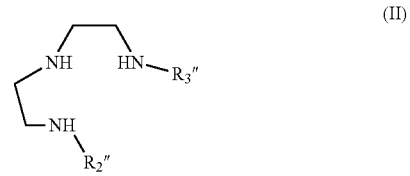

wherein $R_2″$ and $R_3″$ are as defined above, and preferably $\{R_2″, R_3″\}$ represents $\{H, H\}$, $\{H, (CH_2)_2NH_2\}$, $\{(CH_2)_2NH_2, H\}$;

reacts selectively with compound with formula (III)

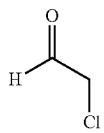
(III)

to form the compound with formula (IV)

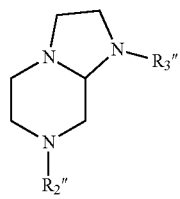
(IV)

wherein $R_2''$ and $R_3''$ are as defined above, preferably $\{R_2'', R_3''\}$ represents $\{H, H\}$, $\{H, (CH_2)_2NH_2\}$, $\{(CH_2)_2NH_2, H\}$;

step (a) being optionally followed by an intermediate step (a'), when $\{R_2'', R_3''\}$ represents $\{H, H\}$, wherein the compound (IV) is put in the presence of $Boc_2O$ to form the compound (IV')

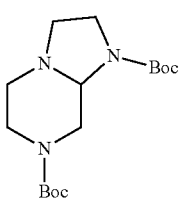
(IV')

a step (b) during which the compound with formula (IV) or (IV') obtained in step (a) or (a') reacts with R1-X wherein R1 and X are as defined above, to form the compound with formula (V).

According to one embodiment, the invention relates to a method for preparation of a compound with formula (V')

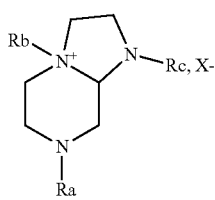
(V')

wherein
X represents a radical selected from bromo, iodo or chloro radicals;
Ra, Rb and Rc are as defined above;
comprising the method for preparation of the compound (V) according to the invention, wherein $\{R_2, R_3\}$ represents $\{Boc, Boc\}$;
and also including a deprotection step in an acid medium, optionally followed by one or several steps (e) that after chemical modifications known to those skilled in the art can result in the compound with formula (V').

According to one embodiment, the invention relates to a method for preparation of a compound with formula (I")

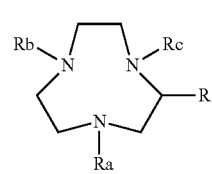
(I")

and its salts, wherein Ra, Rb, Rc and R are as defined above
comprising the method for preparation of the compound with formula (V) or (V') described above
and also comprising step (c) or step (d) below
step (c): step during which the compound with formula (V) obtained in step (b) reacts with a reagent NuM, wherein Nu represents a carbonated nucleophile (carbanion), for example such as CN, alkyl, aryl or malonate and M represents a metallic element, for example such as Na, K, Li or MgX wherein X represents bromo, iodo or chloro, NuM represents for example NaCN to form the compound with general formula (Ia)

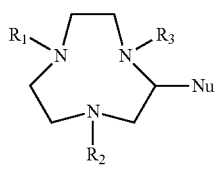
(Ia)

or its salts, wherein $R_1$, $R_2$, $R_3$ and Nu are as defined above;
said step (c) optionally being followed by one or several steps (c') that can lead to the compound with formula (I) as a result of chemical modification(s) known to those skilled in the art

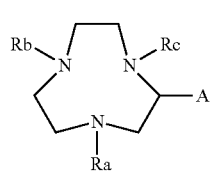
(I)

or its salts, wherein Ra, Rb, Rc and A are as defined above;
step (d): step during which the compound with formula (V) obtained in step (b) reacts with a reducing agent capable of releasing hydrides H—, for example such as NaBH$_4$, LiAlH$_4$, LiAlH(OMe)$_3$, LiAlH(OtBu)$_3$, DIBALH, to form the compound with general formula (I'a)

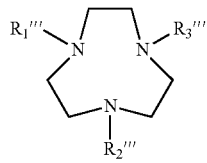
(I'a)

or its salts, wherein R$_1'''$, R$_2'''$ and R$_3'''$ represent R$_1$, R$_2$ and R$_3$ as defined above respectively, or their derivatives formed by reaction with the reducing agent used in step (d);

said step (d) optionally being followed by one or several steps (d') that can lead to the compound with formula (I') after chemical modification(s) known to those skilled in the art

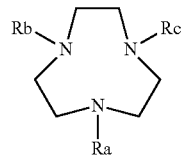
(I')

or its salts, wherein Ra, Rb and Rc are as defined above.

According to a first particular embodiment, the method according to the invention includes the formation of the compound with formula (V-Bn) as a result of steps (a) and (b) described above, corresponding to the compound (V) wherein R$_1$, R$_2$ and R$_3$ are identical and represent an unsubstituted benzyl,

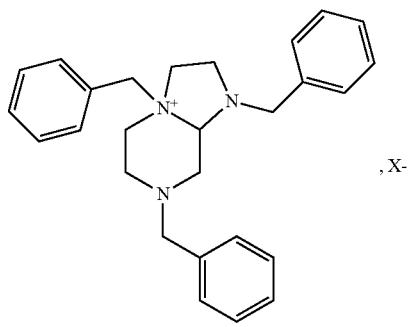
(V-Bn)

or its salts, wherein X is as defined above,
and also includes a reduction step (d) during which the compound (V-Bn) is subjected to a nucleophilic attack by a reducing agent, for example such as sodium borohydride, to obtain the compound with formula (I'a-Bn):

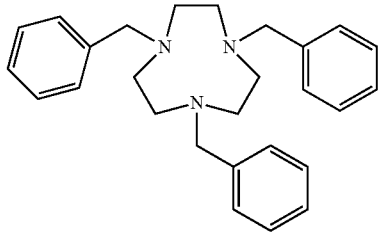
(I'a-Bn)

or its salts.

According to one embodiment, when the method according to the invention leads to the compound with formula (I'a-Bn), the method may also comprise a catalytic hydrogenation step (d'1) then leading to the compound (tacn) corresponding to formula (I') wherein Ra, Rb and Rc are identical and represent a hydrogen atom:

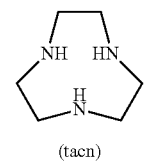
(tacn)

or its salts.

Thus, according to one embodiment of the invention, the synthesis of tacn comprises the steps shown in the following diagram:

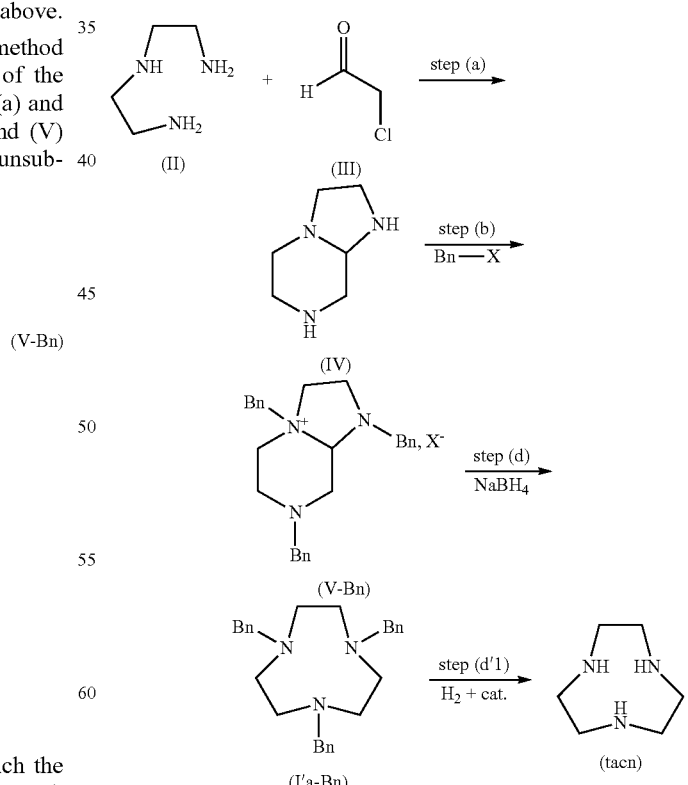

In one embodiment, the method according to the invention leads to the compound (tacn) and also comprises at least one subsequent additional step (d'2) leading to functionalization of three atoms of macrocycle nitrogen, using a method known to those skilled in the art (for example see J. P. L. Cox et al. *J. Chem. Soc., Perkin Trans.* 1990, 2567-2576, A. N. Singh et al., *Bioconjugate Chem.,* 2011, 22, 1650-1662, P. J. Riss et al., *Bioorg. Med. Chem. Lett.,* 2008, 18, 5364-5367, J. Simecek et al., *Inorg. Chem.* 2012, 51, 577-590, Lukes et al, *Chem. Eur. J,* 2010, 16, 714-7185).

According to a second particular embodiment, the method according to the invention leads to the formation of a compound with formula (Ia-i), as a result of steps (a), (b) and (c):

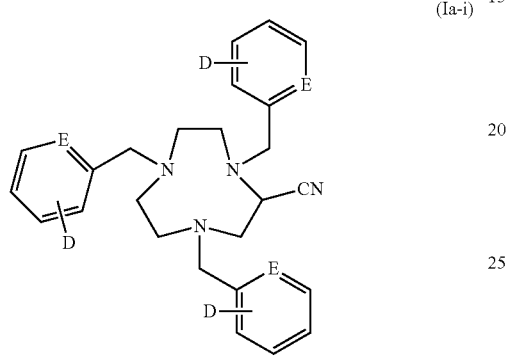

(Ia-i)

or its salts, wherein D represents a hydrogen atom or a radical selected from cyano, nitro, amino radicals, halo (preferably bromo or iodo), alkoxy, (preferably methoxy), hydroxy radicals, and E represents a CH group or a nitrogen atom.

According to one embodiment, when the method according to the invention leads to the compound with formula (Ia-i), the method may also comprise a reduction step (c'1), preferably by aluminium and lithium tetrahydride, then leading to the compound with formula (I-i):

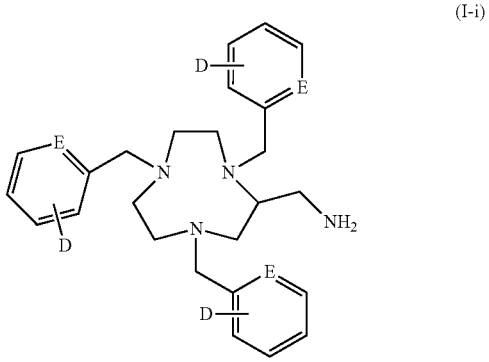

(I-i)

or its salts, wherein D and E are as defined above.

According to one embodiment, when the method according to the invention leads to the compound with formula (I-i), the method may also comprise a subsequent additional step (c'2) during which the $NH_2$ group of (I-i) is functionalized according to an appropriate treatment known to those skilled in the art, for example such as N-alkylation or N-arylation by nucleophilic substitution reactions, a nucleophilic addition or a reducing amination of aldehydes, to form the compound with formula (I-ii):

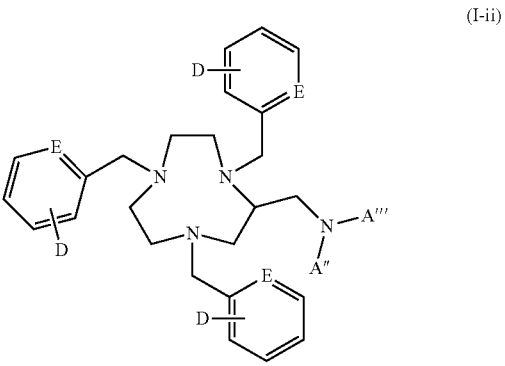

(I-ii)

or its salts, wherein D, E, A" and A'" are as defined above.

According to one particular embodiment, when the method according to the invention leads to the compound with formula (I-i) or the compound (I-ii) wherein D is a hydrogen atom and E is a CH group, the method may also comprise a subsequent additional catalytic hydrogenation step (c'3), leading the compound with formula (I-iii):

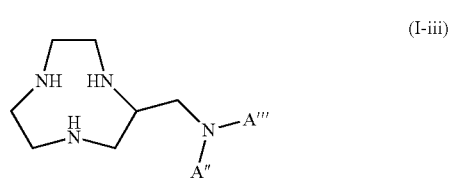

(I-iii)

or its salts, wherein A" and A'" are as defined above.

According to one particular embodiment, when the method according to the invention leads to the compound with formula (I-iii), the method may also comprise a subsequent additional step (c'4) leading to the functionalization of three nitrogen atoms of the macrocycle by the introduction of Ra, Rb and Rc groups as defined previously, by a method known to those skilled in the art (for example see J. P. L. Cox et al. *J. Chem. Soc., Perkin Trans.* 1, 1190, 2567-2576, A. N. Singh et al., *Bioconjugate Chem.,* 2011, 22, 1650-1662, P. J. Riss et al., *Bioorg. Med. Chem. Lett.,* 2008, 18, 5364-5367, J. Simecek et al., *Inorg. Chem.* 2012, 51, 577-590, J. M. Jeong et al., *J. Nucl. Med.* 2008, 49, 830-836), leading to the compound with general formula (I-iv)

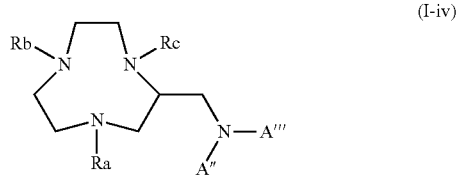

(I-iv)

or its salts, wherein Ra, Rb, Rc, A" and A'" are as defined above.

According to one particular embodiment, the method according to the invention leads to the compound (I-iv) wherein Ra, Rb and Rc are identical and preferably represent:

a —$(CH_2)_n$—C(=O)—$OR'_1$ group wherein $R'_1$ and n are as defined above;

a —(CH$_2$)$_n$—C(=O)—NR'$_1$ group wherein R'$_1$ and n are as defined above; or a —(CH$_2$)$_n$—P(=O)—R'$_2$R'$_3$ group wherein n, R'$_2$ and R'$_3$ are as defined above.

a —CH(COOR'$_4$)(CH$_2$)$_{m4}$COOR'$_5$ group wherein m$_4$, R'$_4$ and R'$_5$ are as defined above.

As illustrated in the following examples, the method according to the invention can be used for direct synthesis of N- and/or C-functionalized triazacyclononanes that represent high added value macrocycles. Target systems are obtained in few steps, starting from commercially available compounds. Unlike syntheses described in prior art, none of the steps in the method according to the invention require any special conditions such as high dilution conditions, use of prolonged treatment in concentrated acid medium, or work under inert atmosphere. Therefore the method according to the invention can be used at large scale.

The mild conditions for the method according to the invention enable the introduction of a very wide variety of organic functions, unlike methods that make use of tosyl groups. Therefore new C-functionalized agents based on triazacyclononane could be prepared using the method according to the invention.

Compounds: C-Functionalized Tacn Derivatives

This invention relates to new macrocyclic compounds derived from 1,4,7-triazacyclononane (tacn) carrying a functional group at a carbon atom of the macrocycle, denoted under the name of "C-functionalized tacn derivatives".

According to one embodiment, the C-functionalized tacn derivatives according to this invention have the general formula (I)

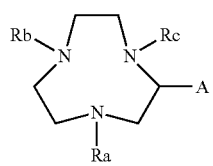

(I)

and its salts, wherein

Ra, Rb and Rc may be identical or different and each represents a hydrogen atom, or a —(CH$_2$)$_n$—R' group wherein n is equal to 0, 1, 2, 3, 4, 5 or 6, n is preferably equal to 0, 1, 2 or 3, and R' represents a saturated or unsaturated, branched or unbranched, substituted or unsubstituted aliphatic group, comprising 1 to 12 carbon atoms, preferably, when the aliphatic group is substituted, it is by one or several substituents, selected from the group comprising halo, hydroxyl, oxo, nitro, amido, carboxy, amino, cyano, haloalkoxy, haloalkyl;

when n is equal to 0, R' represents —CH(COOR'$_4$)(CH$_2$)$_{m4}$COOR'$_5$ wherein m$_4$ is equal to 1, 2 or 3 and R'$_4$, R'$_5$ are identical or different and each represent a hydrogen atom or a group selected from alkyl, benzyl, paranitrobenzyl, pentafluorobenzyl, N-hydrosuccinimide (NHS), sulfo-NHS group; preferably m$_4$ is equal to 2, R'$_4$ represents tBu and R'$_5$ represents H;

an unsubstituted benzyl group or a benzyl group substituted in the meso and/or meta and/or para and/or ortho position by one or several radicals selected from cyano, nitro, amino, halo, alkoxy, hydroxy radicals;

an unsubstituted methyl pyridine group or a methyl pyridine group substituted by one or several groups selected from cyano, nitro, amino, halo, alkoxy, hydroxy groups;

an aromatic group, preferably selected from the group comprising phenyl, biphenyl, 1-naphthyl, the 2-naphthyl, anthracenyl, pyrenyl, tetrahydronaphthyl, indanyl, binaphthyl, terpyridinyl, bipyridinyl, guanine, phenantroline, hydroxyquinoline and quinoline group, more preferably a quinoline group;

a SH group;

a —C(=O)—OR'$_1$ group wherein R'$_1$ represents a hydrogen atom or a saturated or unsaturated, branched or unbranched, substituted or unsubstituted aliphatic group, comprising 1 to 12 carbon atoms, wherein when the aliphatic group is substituted, it is by one or several substituents, selected from the group comprising halo, hydroxyl, oxo, nitro, amido, carboxy, amino, cyano, haloalkoxy, haloalkyl, aryl, and preferably R'$_1$ represents a hydrogen atom or a methyl, ethyl, tert-butyl, benzyl, paranitrobenzyl, pentafluorobenzyl, N-hydrosuccinimide (NHS), or sulfo-NHS group;

a —(CH$_2$)$_2$—OR'$_1$ group wherein R'$_1$ is as defined above;

a —C(=O)—NHR'$_1$ group wherein R'$_1$ is as defined above;

a —C(=O)—SR'$_1$ group wherein R'$_1$ is as defined above; preferably R'$_1$ represents a benzyl, methyl or phenyl;

a —P(=O)—R'$_2$R'$_3$ group wherein R'$_2$ and R'$_3$ may be identical or different and each represents a —(CH$_2$)$_{m1}$—R''$_1$ group wherein m$_1$ is equal to 0, 1, 2, 3, 4, 5 or 6, preferably equal to 0, 1, 2 or 3 and R''$_1$ represents a saturated or unsaturated aliphatic chain, possibly interrupted by one or several oxygen, nitrogen or sulphur atoms; preferably R''$_1$ represents a —(CH$_2$)$_{m2}$—OR'$_1$ group wherein m$_2$ is equal to 0, 1, 2, 3, 4, 5 or 6, preferably equal to 0, 1, 2 or 3 and R'$_1$ is as defined above, preferably ethoxy, OH;

a —(CH$_2$)$_{m3}$—C(=O)—OR'$_1$ group wherein m$_3$ is equal to 1, 2, 3 or 4 and R'$_1$ is as defined above;

an alkyl group comprising 1 to 12 carbon atoms, preferably a methyl;

A represents a —(CH$_2$)$_{w1}$-A' group wherein w$_1$ is equal to 0, 1, 2, 3 or 4, preferably w$_1$ is equal to 0 or 1, and A' represents a saturated or unsaturated, branched or unbranched, substituted or unsubstituted aliphatic group comprising 1 to 12 carbon atoms;

a cyano group; A' preferably represents a cyano group when w$_1$ is equal to 0;

an aliphatic or aromatic group containing a function that can lead to click chemistry reactions, and more particularly a group containing an azide, alkyne, cyclooctene or 1,2,4,5 tetrazine function;

an unsubstituted benzyl group or a benzyl group substituted in the meso and/or meta and/or para and/or ortho position by one or several groups selected from cyano, nitro, amino, halo, alkoxy, hydroxy groups;

an unsubstituted methyl pyridine group or a methyl pyridine group substituted by one or several groups selected from cyano, nitro, halo, alkoxy, hydroxy groups;

an aromatic group, preferably selected from the group comprising phenyl, biphenyl, 1-naphthyl, the 2-naphthyl, anthracenyl, pyrenyl, tetrahydronaphthyl, indanyl, binaphthyl, terpyridinyl, bipyridinyl, guanine, phenantroline, hydroxyquinoline and quinoline group;

a $(CH_2)_{w2}$—NA"A'" group wherein $w_2$ is equal to 0, 1, 2, 3 or 3, preferably $w_2$ is equal to 0, 1, 2 or 3, and more preferably $w_2$ is equal to 1, and wherein A" and A'" are identical or different and each represents a hydrogen atom;

a saturated or unsaturated, branched or unbranched, substituted or non-substituted aliphatic group, comprising 1 to 12 carbon atoms, preferably, when the aliphatic group is substituted, it is by one or several substituents, selected from the group comprising halo, hydroxyl, oxo, nitro, amido, carboxy, amino, cyano, haloalkoxy, haloalkyl;

a —$(CH_2)_{w3}$-A"$_1$ group wherein $w_3$ is equal to 0, 1, 2, 3, 4, 5 or 6, preferably equal to 0, 1, 2 or 3 and A"$_1$ represents a saturated or unsaturated, branched or unbranched, substituted or unsubstituted aliphatic chain that can contain 1 to 4 (C═O) or (C═S) or (P═O) motifs and/or one or several heteroatoms, one or several meta and/or para and/or ortho substituted aromatic rings; preferably A"$_1$ represents a —$(CH_2)_{w4}$—C(═O)-A'"$_1$ group wherein $w_4$ is equal to 0, 1, 2, 3, 4, 5 or 6, and $w_4$ is preferably equal to 0 or 1, and A'"$_1$ represents an —OY group wherein Y represents a hydrogen, a branched or unbranched alkyl group, a substituted or unsubstituted benzyl group or a succinimide derivative, preferably Y represents a hydrogen, or a methyl, ethyl, tert-butyl, benzyl, paranitrobenzyl, pentafluorobenzyl, N-hydrosuccinimide (NHS), sulfo-NHS group;

a saturated or unsaturated, branched or unbranched aliphatic group comprising 1 to 12 carbon atoms, preferably a methyl group;

a benzyl group substituted in the para position by a group selected from cyano, nitro, isothiocyanate, amino, alkoxy groups;

preferably, the —$(CH_2)_{w3}$-A"$_1$ group is a —$CH_2$—C(═O)—OH, —$CH_2$C(═O)-OtBu, —$CH_2$—P(═O)-(Me)OCH$_2$CH$_2$COOH, —CH$_2$PhOCH$_2$C≡CH, —C(═O)CH$_2$CH$_2$COOH, —C(═O)—CH$_2$PhNO$_2$, —C(═O)—CH$_2$PhNH$_2$ or —C(═O)CH$_2$PhNCS group;

a —C(═O)—Z group wherein Z represents an organic fluorescent motif, for example such as fluorescein, rhodamine, polymethine, boron dipyrromethene, porphyrine, phthalocyanine, squaraine or a derivative of these groups;

a —C(═O)—Z' group wherein Z' contains a macrocyclic or bismacrocyclic moiety;

a —C(═O)—Z" group wherein Z" contains an organometallic moiety

A" and A'" form together an anhydride ring such that $(CH_2)_{w2}$—NA"A'" is of formula:

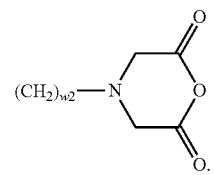

According to one embodiment, the compounds with general formula (I) are as defined above, with the condition that:

when Ra, Rb and Rc are identical and represent hydrogen atoms, then A is not Me, iPr, CH$_2$Bz, CH$_2$NHBz, (CH$_2$)$_4$NHBz, CH$_2$Ph, CH$_2$PhNH$_2$, CH$_2$Ph(p-NO$_2$), CH$_2$Ph(p-NHCOPh), CH$_2$PhNCS, CH$_2$PhCOPh, or (CH$_2$)$_4$NHCOPh;

when Ra, Rb and Rc are identical and represent methyls, then A is not Me, (CH$_2$)$_9$CH$_3$, CN, CH$_2$NH$_2$, CH$_2$NHBoc, CH$_2$NHAc, CH$_2$Ph or iPr;

when Ra, Rb and Rc are identical and represent the CH$_2$COOEt groups, then A is not (CH$_2$)$_4$NHCOPh or (CH$_2$)$_4$NHBz;

when Ra, Rb and Rc are identical and represent CH$_2$COOtBu groups, then A is not CH$_2$Ph(p-NO$_2$);

when Ra, Rb and Rc are identical and represent CH$_2$COOH, then A is not CH$_2$Ph(p-NCS), CH$_2$Ph(p-NO$_2$), CH$_2$Ph(p-NH$_2$), CH$_2$Ph(p-NHCOCH$_2$Br), CH$_2$Ph(p-NHCOPh), (CH$_2$)$_4$NH$_2$, (CH$_2$)$_4$NHBz, Ph(p-NCS), butyl-N-2-((6-vinylpyridin-2-yl)methoxy)acetamide, CH$_2$Ph(p-NHC(S)NH-D-Ala-D-Lys(HSG)-D-Tyr-D-Lys(HSG)-NH$_2$;

when Ra, Rb and Rc are identical and represent CH$_2$COOH, then A is not a benzyl group substituted in para position by a thiourea derivative.

In a specific embodiment, A' does not represent a saturated or unsaturated, branched or unbranched, substituted or unsubstituted aliphatic group comprising 1 to 12 carbon atoms.

In a specific embodiment, A is not a benzyl group substituted in para position by a thiourea derivative.

According to one particular embodiment, A is not a benzyl or an alkyl group comprising 1 to 8 carbon atoms. According to one particular embodiment, when Ra, Rb and Rc are identical or different and represent —(CH$_2$)$_n$—R' wherein R' represents an aliphatic group, a substituted or unsubstituted benzyl group, a substituted or unsubstituted methylpyridine group, —(CH$_2$)$_2$—OR'$_1$, then A is not a benzyl or an alkyl group comprising 1 to 8 carbon atoms.

According to one particular embodiment, when compounds with general formula (I) are salts and Ra, Rb and Rc are identical or different and represent a hydrogen atom or a substituted or unsubstituted alkyl group, then A is not a substituted or unsubstituted alkyl group.

According to one embodiment, compounds with general formula (I) are salts and in this case the counter ion is preferably derived from Cl, Br, I, TFA (trifluoroacetic acid).

According to one embodiment, compounds with general formula (I) may be obtained by the method according to this invention.

Compounds with formula (I) according to this invention are composed of a cyclic core comprising three nitrogen atoms connected in pairs by an ethylene motif and a functional group A carried by the carbon skeleton. The three nitrogen atoms may be substituted or unsubstituted by groups Ra, Rb and Rc. According to one particular embodiment, Ra, Rb and Rc are coordinating groups that can complete the coordination sphere when a metallic ion is incorporated.

Compounds according to this invention have the advantages of C-functionalization of nitrogen-containing macrocycle ligands, namely they offer the possibility of introducing a new functionality on the macrocyclic molecule while maintaining the three groups Ra, Rb and Rc to complete the coordination sphere of the metal that can be complexed.

According to one embodiment, the compounds according to the invention have the general formula (Ia):

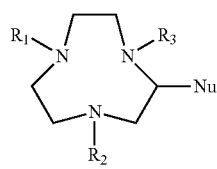

(Ia)

and its salts, wherein
R$_1$ represents a (CH$_2$)$_p$—B radical wherein
  p is equal to 1, 2, 3 or 4;
  B represents
    a hydrogen atom;
    an unsubstituted phenyl radical or a phenyl radical substituted in the meta and/or para and/or ortho position by one or several radicals selected from cyano, nitro, amino, halo (preferably bromo or iodo), alkoxy (preferably methoxy), hydroxy radicals;
    an unsubstituted pyridine radical or a pyridine radical substituted by one or several radicals selected from cyano, nitro, amino, halo (preferably bromo or iodo) alkoxy (preferably methoxy), hydroxy radicals;
R$_2$ represents R$_1$, R$_2$", R$_2$" modified by reaction with R$_1$—X or a Boc group,
  where R$_2$" represents a hydrogen atom or an aliphatic or aromatic group, optionally substituted by one or several radicals selected from
and its salts, wherein A is as defined in formula (I). cyano, nitro, amino, halo, alkoxy, hydroxy radicals, R$_2$" preferably represents H or —(CH$_2$)$_2$NH$_2$;
R$_2$ preferably represents R$_1$ or (CH$_2$)$_2$N(R$_1$)$_2$;
R$_3$ represents R$_1$, R$_3$", R$_3$" modified by reaction with R$_1$—X or a Boc group,
  where R$_3$" represents a hydrogen atom or an aliphatic or aromatic group, optionally substituted by one or several radicals selected from cyano, nitro, amino, halo, alkoxy, hydroxy radicals, preferably R$_3$" represents H or —(CH$_2$)$_2$NH$_2$;
R$_3$ preferably represents R$_1$ or (CH$_2$)$_2$N(R$_1$)$_2$;
{R$_2$, R$_3$} preferably represents {R$_1$, R$_1$}, {R$_1$, (CH$_2$)$_2$N(R$_1$)$_2$}, {(CH$_2$)$_2$N(R$_1$)$_2$, R$_1$} or {Boc, Boc};
Nu represents a carbonated nucleophilic group, Nu for example represents CN, an alkyl group, an aryl group or a malonate group.

According to one embodiment, compounds according to the invention have a general formula (Ib):

(Ib)

and its salts, wherein A is as defined in formula (I).

According to one embodiment, the preferred compounds with formula (Ib) are compounds wherein A represents a —(CH$_2$)$_{w_2}$—NA"A'" group wherein w$_2$, A" and A'" are as defined above; A preferably represents a —(CH$_2$)—NA"A'" group and in this case has a specific formula (I-iii).

According to one embodiment, the compounds according to the invention have the general formula (Ic):

(Ic)

and its salts, wherein A, n and R' are as defined in formula (I).

According to one embodiment, preferred compounds with formula (Ic) are compounds wherein n is equal to 1 and R' represents a —C(=O)—OR'$_1$ group wherein R'$_1$ represents a hydrogen atom or a saturated or unsaturated, branched or unbranched, substituted or unsubstituted aliphatic group comprising 1 to 12 carbon atoms, preferably R'$_1$ represents a hydrogen atom or a methyl, ethyl or tert-butyl group.

According to one embodiment, preferred compounds with formula (Ic) are compounds wherein n is equal to 1 and R' represents a —P(=O)—R'$_2$R'$_3$ group wherein R'$_2$ and R'$_3$ may be identical or different and each represents a —(CH$_2$)$_{m_1}$—R"$_1$ group wherein m$_1$ is as defined above and R"$_1$ represents a saturated or unsaturated aliphatic chain, possibly interrupted by one or several oxygen, nitrogen or sulphur atoms; R"$_1$ preferably represents a methyl, ethyl, methoxy, ethoxy group; R'$_1$ preferably represents P(=O)-Me(OEt).

According to one embodiment, preferred compounds with formula (Ic) are compounds wherein n is equal to 0 and R' represents an unsubstituted benzyl group or a benzyl group substituted in the meso and/or meta and/or para and/or ortho position by one or several radicals selected from cyano, nitro, amino, halo (preferably bromo, iodo or fluoro), alkoxy (preferably methoxy), hydroxy radicals; R' preferably represents an unsubstituted benzyl group.

According to one embodiment, preferred compounds with formula (Ic) are compounds wherein n is equal to 0 and R' represents an unsubstituted methyl pyridine group or a methyl pyridine group substituted par one or several groups selected from cyano, nitro, amino, halo (preferably bromo or iodo), alkoxy (preferably methoxy), hydroxy groups; R' preferably represents an unsubstituted methyl pyridine group.

According to one embodiment, preferred compounds with formula (Ic) are compounds wherein n is equal to 0, R' represents a benzyl group or a methyl pyridine group, said groups being unsubstituted or substituted by one or several groups selected from cyano, nitro, amino, halo (preferably bromo or iodo) alkoxy (preferably methoxy) groups, and A represents a —(CH$_2$)NH$_2$ group represented by the specific formula (I-i).

According to one embodiment, preferred compounds with formula (Ic) are compounds wherein n is equal to 0, R' represents a benzyl group or a methyl pyridine group, said groups being unsubstituted or substituted by one or several groups selected from cyano, nitro, amino, halo (preferably bromo or iodo) alkoxy (preferably methoxy) groups, and A represents a —(CH₂)NA"A" group wherein A" and A'" are as defined above, represented by the specific formula (I-ii).

According to one embodiment, preferred compounds with formula (Ic) are compounds wherein n is equal to 0, R' represents an unsubstituted benzyl or methyl pyridine group, substituted by one or several groups selected from cyano, nitro, amino, halo (preferably bromo or iodo), alkoxy (preferably methoxy) groups, and A represents a cyano group, represented by the specific formula (Ia-i).

According to one embodiment, compounds according to the invention have the general formula (Id):

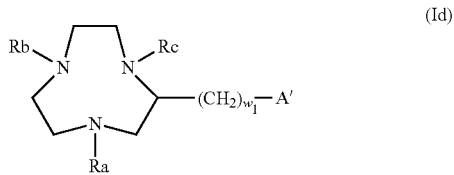

(Id)

and its salts, wherein Ra, Rb, Rc, $w_1$ and A' are as defined in formula (I).

According to one embodiment, preferred compounds with formula (Id) are compounds wherein $w_1$ is equal to 0 and A' represents a cyano group.

According to one embodiment, preferred compounds with formula (Id) are compounds wherein $w_1$ is equal to 0, A' represents a cyano group and Ra, Rb and Rc are identical and represent —(CH₂)ₙ—R' group wherein n is preferably equal to 0 and R' represents an unsubstituted benzyl group or a benzyl group substituted in the meso and/or meta and/or para and/or ortho position by one or several radicals selected from cyano, nitro, amino, halo (preferably bromo, iodo or fluoro), alkoxy (preferably methoxy), hydroxy radicals; more preferably R' represents an unsubstituted benzyl group.

According to one embodiment, the compounds according to the invention have the general formula (Ie):

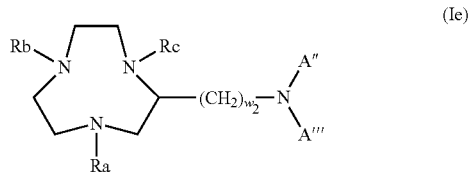

(Ie)

and its salts, wherein Ra, Rb, Rc, $w_2$, A" and A'" are as defined in formula (I).

According to one embodiment, preferred compounds with formula (Id) are compounds wherein $w_2$ is equal to 1, represented by the specific formula (I-iv).

According to one embodiment, preferred compounds with formula (Id) are compounds wherein $w_2$ is equal to 1 and A" represents a hydrogen atom and A'" represents a —C(=O)—Z group wherein Z represents an organic fluorescent motif, for example such as fluorescein, rhodamine, polymethine, boron dipyrromethene, porphyrin, phthalocyanine, squaraine or a derivative of these groups; preferably Z represents a boron dipyrromethene group.

According to one particular embodiment, compounds (I) according to the invention are such that Ra, Rb and Rc are identical and represent CH₂COOH, CH₂COOtBu, CH₂COOEt, CH₂P(=O)(Me)OH or CH₂P(=O)(Me)OEt type groups and A is a —CH₂NH₂ function. The possibly activated —CH₂NH₂ function can be used to couple the macrocycle to a solid support or a biological support, making use of chemical reactions known to those skilled in the art, for example such as an N-alkylation or N-arylation by nucleophilic substitution reactions, a nucleophilic addition or a reducing amination of aldehydes. Especially, the —CH₂NH₂ function, not modified, or modified with a suitable functional group, can react with NH₂, SH, COOH, OH, azide, alkyne functions or other reactive functions present on the solid or biological support to be functionalized. By "suitable functional group", it is referred to reactive functions such as for example activated esters, maleimide, azide, alkyne, vinylsulfone or thioctic acid. "Biological support" means entire antibody type biological molecules, fragments of antibodies, peptides, oligonucleotides, aptamers or recombining proteins. According to one particular embodiment, the biological molecule is not folate or a derivative of folate. "Solid support" means silica gel or an organic polymer. Labeling of nanoparticles is also possible. The possibly activated —CH₂NH₂ function can also be used to couple the macrocycle to another macrocycle, bismacrocycle, fluorescent dye, or organometallic complex, using chemical reactions known to those skilled in the art, such as for example an N-alkylation or N-arylation by nucleophilic substitution reactions, a nucleophilic addition or a reducing amination of aldehydes.

In one embodiment, one or more biological supports, as defined above, are linked to the macrocycle of the present invention. In a specific embodiment, one, two or more peptides are linked to a macrocycle according to the invention.

In an embodiment, the invention relates to compounds with general formula (I) coupled to a solid support such as for example silica gel, organic polymer, nanoparticle; or to a biological support such as for example entire antibody type biological molecules, fragments of antibodies, peptides, oligonucleotides, aptamers or recombining proteins.

In one particular embodiment, the following compounds comply with formula (I) according to the invention:
1,4,7-tribenzyl-1,4,7-triazacyclononane-2-carbonitrile (4)
(1,4,7-tribenzyl-1,4,7-triazacyclononan-2-yl) methanamine (5)
(1,4,7-triazacyclononan-2-yl) methanamine (6)
tert-butyl (1,4,7-tribenzyl-1,4,7triazacyclononan-2-yl) methyl)carbamate (7)
tert-butyl ((1,4,7-triazacyclononan-2-yl)methyl)carbamate (8)
tert-butyl ((1,4,7-tris((ethoxy(methyl)phosphoryl)methyl)-1,4,7-triazacyclononan-2-yl)methyl)carbamate (9)
(2-(aminomethyl)-1,4,7-triazacyclononane-1,4,7-triyl)tris (methylene))tris(methylphosphinic acid) (10)
((2-(acetamidomethyl)-1,4,7-triazacyclononane-1,4,7-triyl) tris(methylene)) tris(methylphosphinic acid) (11)
tri-tert-butyl-2,2',2"-(2-((bis(2-(tert-butoxy)-2-oxoethyl) amino)methyl)-1,4,7-triazacyclononane-1,4,7-triyl)triacetate (12)
2,2',2"-(2-((bis(carboxymethyl)amino)methyl)-1,4,7-triazacyclononane-1,4,7-triyl)triacetic acid (13)
N-((1,4,7-triazacyclononan-2-yl)methyl)-1-(4-(prop-2-yn-1-yloxy)phenyl) methanamine (15)
tri-tert-butyl-2,2',2"-(2-(((4-(prop-2-yn-1-yloxy)benzyl) amino)methyl)-1,4,7-triazacyclononane-1,4,7-triyetriacetate (16)
(1,4,7-triazacyclononan-2-yl)-BODIPY (17)
2,2',2"-(2-(((tert-butoxycarbonyl)amino)methyl)-1,4,7-triazacyclononane-1,4,7-triyl)triacetate (25)

2,2',2"-(2-(aminomethyl)-1,4,7-triazacyclononane-1,4,7-triyl)triacetic acid (26)

2,2',2"-(2-((2-(4-nitrophenyl)acetamido)methyl)-1,4,7-triazacyclononane-1,4,7-triyl)triacetic acid (27)

2,2',2"-(2-((2-(4-aminophenyl)acetamido)methyl)-1,4,7-triazacyclononane-1,4,7-triyl)triacetic acid (28)

2,2',2"-(2-((2-(4-isothiocyanatophenyl)acetamido)methyl)-1,4,7-triazacyclononane-1,4,7-triyl)triacetic acid (29)

((2-((2-(4-isothiocyanatophenyl)acetamido)methyl)-1,4,7-triazacyclononane-1,4,7-triyl)tris(methylene))tris(methylphosphinic acid) (30)

and their salts.

In another aspect, the invention also relates to macrocyclic metallic complexes deriving from compounds with formula (I). According to one embodiment, the metallic complex according to the invention comprises a ligand with formula (I) according to the invention, and a metal, preferably in the form of a bi-, tri or tetravalent ion, chosen from the group comprising Zn, Ca, Be, Mg, Sr, Cu, Ba, Cd, Cr, Mn, Fe, Co, Ni, Al, Ga, In, Zr, Tc, Gd, Y, Lu, At, Pb, Sc, Tb, Eu, Yb, Ru, Rh, other lanthanides or one of their radioactive isotopes. Examples of radioactive isotopes are $^{67}$Ga, $^{68}$Ga, $^{64}$Cu, $^{67}$Cu, $^{90}$Y, $^{111}$In, $^{89}$Zr, $^{99m}$Tc, $^{177}$Lu, $^{211}$At, $^{212}$Pb. According to one embodiment, the complexed metal is preferably an ion derived from the Al, In, Ga, Zr and Cu metals. According to one embodiment, the complexed metal in the macrocyclic cavity is preferably a bi, tri or tetravalent ion such as for example the $Zn^{2+}$, $Ca^{2+}$, $Be^{2+}$, $Mg^{2+}$, $Sr^{2+}$, $Cu^{2+}$, $Ba^{2+}$, $Cd^{2+}$, $Cr^{2+}$, $Mn^{2+}$, $Fe^{2+}$, $Co^{2+}$, $Ni^{2+}$, $Al^{3+}$, $Ga^{3+}$, $In^{3+}$, $Cr^{3+}$, $Mn^{3+}$, $Fe^{3+}$, $Zr^{4+}$ ions.

When the macrocyclic metallic complex derived from compounds with formula (I) is used for PET imaging, the complexed metal is preferably $^{68}$Ga, $^{64}$Cu, $^{21}$Sc or $^{89}$Zr, $^{152}$Tb, $^{44}$Sc. The metal may also be Al to enable labeling with $^{18}$F for PET imaging.

When the macrocyclic metallic complex derived from compounds with formula (I) is used for the SPECT imaging, the complexed metal is preferably $^{111}$In, $^{99m}$Tc or $^{67}$Ga, $^{155}$Tb.

When the macrocyclic metallic complex derived from compounds with formula (I) is used for radiotherapy, preferably radioimmunotherapy, the complexed metal is preferably $^{90}$Y, $^{177}$Lu, $^{211}$At, $^{212}$Pb, $^{21}$Sc or $^{64/67}$Cu.

When the macrocyclic metallic complex derived from compounds with formula (I) is used for MRI, the complexed metal is preferably Gd or Mn.

When the macrocyclic metallic complex derived from compounds with formula (I) is used for fluorescence imaging or PARACEST MRI, the complexed metal is preferably a lanthanide, and even more preferably Tb, Eu or Yb.

Compounds: Salts of imidazo[1,2-a]pyrazin-4-ium

The invention also relates to compounds with formula (V')

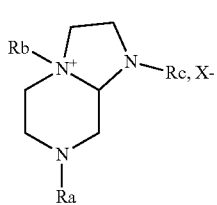

(V')

X represents a radical selected from bromo, iodo or chloro radicals;

Ra, Rb and Rc may be identical or different and each represents a hydrogen atom, or a —$(CH_2)_n$—R' group wherein n is equal to 0, 1, 2, 3, 4, 5 or 6, n is preferably equal to 0, 1, 2 or 3 and R' represents a saturated or unsaturated, branched or unbranched, substituted or unsubstituted aliphatic group, comprising 1 to 12 carbon atoms, preferably when the aliphatic group is substituted, it is by one or several substituents, selected from the group comprising halo, hydroxyl, oxo, nitro, amido, carboxy, amino, cyano, haloalkoxy, haloalkyl;

when n is equal to 0, R' represents —$CH(COOR'_4)$ $(CH_2)_{m4}COOR'_5$ wherein $m_4$ is equal to 1, 2 or 3 and $R'_4$, $R'_5$ are identical or different and each represent a hydrogen atom or a group selected from alkyl, benzyl, paranitrobenzyl, pentafluorobenzyl, N-hydrosuccinimide (NHS), sulfo-NHS group; preferably $m_4$ is equal to 2, $R'_4$ represents tBu and $R'_5$ represents H;

an unsubstituted benzyl group or a benzyl group substituted in the meso and/or meta and/or para and/or ortho position by one or several radicals selected from cyano, nitro, amino, halo, alkoxy, hydroxy radicals;

an unsubstituted methyl pyridine group or a methyl pyridine group substituted by one or several groups selected from cyano, nitro, amino, halo, alkoxy, hydroxy groups;

an aromatic group, preferably selected from the group comprising phenyl, biphenyl, 1-naphthyl, the 2-naphthyl, anthracenyl, pyrenyl, tetrahydronaphthyl, indanyl, binaphthyl, terpyridinyl, bipyridinyl, guanine, phenantroline, hydroxyquinoline and quinoline group, more preferably a quinoline group;

a SH group;

a —C(=O)—$OR'_1$ group wherein $R'_1$ represents a hydrogen atom or a saturated or unsaturated, branched or unbranched, substituted or unsubstituted aliphatic group, comprising 1 to 12 carbon atoms, wherein when the aliphatic group is substituted, it is by one or several substituents, selected from the group comprising halo, hydroxyl, oxo, nitro, amido, carboxy, amino, cyano, haloalkoxy, haloalkyl, aryl and preferably $R'_1$ represents a hydrogen atom or a methyl, ethyl, tert-butyl, benzyl, paranitrobenzyl, pentafluorobenzyl, N-hydrosuccinimide (NHS), sulfo-NHS group;

a —$(CH_2)_2$—$OR'_1$ group wherein $R'_1$ is as defined above;

a —C(=O)—$NHR'_1$ group wherein $R'_1$ is as defined above;

a —C(=O)—$SR'_1$ group wherein $R'_1$ is as defined above; preferably $R'_1$ represents a benzyl, methyl or phenyl;

a —P(=O)—$R'_2R'_3$ group wherein $R'_2$ and $R'_3$ may be identical or different and each represents a —$(CH_2)_{m1}$—$R''_1$ group wherein $m_1$ is equal to 0, 1, 2, 3, 4, 5 or 6, preferably equal to 0, 1, 2 or 3 and $R''_1$ represent a saturated or unsaturated aliphatic chain, possibly interrupted by one or several oxygen, nitrogen or sulphur atoms; preferably $R''_1$ represents a —$(CH_2)_{m2}$—$OR'_1$ group wherein $m_2$ is equal to 0, 1, 2, 3, 4, 5 or 6, preferably equal to 0, 1, 2 or 3 and $R'_1$ is as defined above, preferably ethoxy, OH;

a —$(CH_2)_{m3}$—C(=O)—$OR'_1$ group wherein $m_3$ is equal to 1, 2, 3 or 4 and $R'_1$ is as defined above;

an alkyl group comprising 1 to 12 carbon atoms, preferably a methyl.

According to one embodiment, the compounds with formula (V') are as defined above, with the condition that Ra, Rb and Rc are not simultaneously three methyl groups.

In one preferred embodiment, Ra and Rc represent (C=O)OtBu type groups and Rb an alkyl or benzyl type group. This embodiment in particular can access systems selectively N-functionalized by successive reactions available to those skilled in the art.

Use of Compounds According to the Invention

As mentioned previously, the (I") compounds and particularly the compounds with formula (I) according to this invention can act as ligands to form a metallic complex.

According to one embodiment, compounds with formula (I"), and particularly formula (I) according to the invention may be used as chelating agents for the treatment of liquids, particularly to eliminate traces of metallic elements. In particular, compounds with formula (I") according to the invention may be used for decontamination of radioactive effluents and elimination of toxic heavy metals.

According to one embodiment, compounds with formula (I"), particularly formula (I) according to the invention may be used for the production of new coordination polymers of the MOF ("Metal-Organic Framework") type that selectively trap specific gases. These three-dimensional systems may be prepared by self-assembly of polycarboxylic molecular bricks with formula (I").

According to one embodiment, metallic complexes derived from compounds with formula (I"), particularly formula (I), may be used as catalysts. In particular they may be used as catalysts in epoxidation reactions, particularly asymmetric epoxidation reactions.

According to one embodiment, metallic complexes derived from compounds with formula (I"), particularly formula (I), may be used as imaging and/or radiotherapy agents, or used in radioimmunotherapy or in theranostic. Thus, the invention also relates to the use of complexes according to the invention for imaging by single photon emission computed tomography (SPECT), positron emission tomography (PET) or magnetic resonance imaging (MRI).

According to one embodiment, metallic complexes derived from compounds with formula (I"), particularly formula (I), may be used in multimodal imaging such as for example SPECT/optical imaging (OI), PET/OI, PET/MRI, SPECT/MRI, MRI/OI.

According to one embodiment, the metallic complexes derived from compounds with formula (I"), particularly formula (I), may be used as biological molecule markers particularly as peptide or antibody markers.

This invention also relates to compounds obtained by coupling biological molecules with a ligand with formula (I) according to the invention that may or may not be complexed with a metal. When coupling the ligand according to the invention with a biological molecule, a spacer group may be used between the ligand and the biological molecule. According to one embodiment, the spacer may for example be a PEG group.

EXAMPLES

This invention will be better understood after reading the following examples that provide non-limitative illustrations of the invention.

Example A: Preparation of Compound 1,4,7-triazacyclononane (Tacn) (3)

1 Preparation of the Reactional Intermediary octahydroimidazol[1,2-a]pyrazine

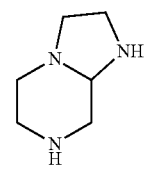

(1)

A solution of chloroacetaldehyde (50% in $H_2O$, 98.8 g, 0.63 mol) in 500 mL of acetonitrile are added drop by drop at 20° C. to a solution of diethylenetriamine (64.9 g, 0.63 mol) and $K_2CO_3$ (1.23 mol, 173.9 g, 2 eq) in 1 L of acetonitrile. The mix is stirred at ambient temperature for 6 h. After filtration on celite, the solvent is evaporated. 800 mL of diethyl ether are added onto the residual oil, non-soluble impurities are eliminated by filtration. After evaporation of the solvent, the compound 1 is obtained in the form of a yellow oil (m=56.8 g, yield=71%). $^1$H NMR (300 MHz, CDCl$_3$, 298 K) δ (ppm): 1.60-1.81 (bs, 2H, NH); 1.93-2.04 (m, 2H); 2.23 (dd, 1H, $^2$J=11.6 Hz, $^3$J=8.0 Hz, CH$_2$CH); 2.43-2.45 (m, 2H); 2.56-2.63 (m, 3H); 2.73-2.77 (m, 2H); 2.87 (dd, 1H, $^2$J=11.6, $^3$J=2.6 Hz, CH$_2$CH). $^{13}$C{$^1$H} NMR (75 MHz, CDCl$_3$, 298 K) δ(ppm): 42.1; 44.3; 48.4; 50.2 51.6 (CH$_2$); 75.7 (CH).

2 Preparation of the Reactional Intermediary 1,4,7-tribenzyl-1,4,7-triazacyclononane

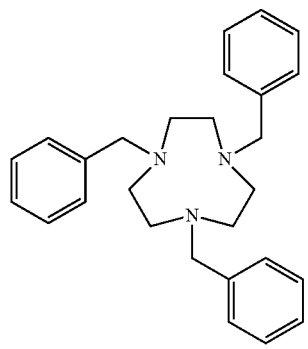

(2)

353.9 g of benzyl bromide (2.06 mol, 3 equivalents) are added drop by drop at 10° C. to a solution of 1 (87.61 g, 0.69 mol) and 380 g of potassium carbonate (2.76 mol, 4 equivalents) in 1.8 L of acetonitrile. The mix is stirred at ambient temperature for 24 h. After filtration on celite, the solvent is evaporated, and 1.8 L of ethanol are added on the residual oil. 26 g of sodium borohydride (0.69 mol, 1 equivalent) are added at −10° C. After 12 hours, the solvent is evaporated and oil is dissolved in chloroform and ether. The solvent is evaporated and oil is dissolved in ethanol (200 mL) and 100 mL of hydrochloric acid are added. The mix is evaporated to dry and 500 mL of acetone are added on the residual oil, the white precipitate formed is isolated by filtration and then recrystallised in water (400 mL). The crystals are filtered, a solution of 13 M NaOH is added slowly until pH>12 is reached. After extraction with chloroform, the organic phase is dried on MgSO$_4$. After filtration and evaporation of the solvent, the compound 2 is obtained in the form of a colourless oil (m=102 g, yield=37%). $^1$H NMR (300 MHz, CDCl$_3$, 300 K) δ(ppm): 2.86 (s, 12H); 3.65 (s, 6H); 7.28-7.36 (m, 15H). $^{13}$C{$^1$H} NMR (75 MHz, CDCl$_3$, 300 K) δ(ppm): (CH$_2$) 55.4 (*6); (CH$_2$) 63.0 (*3); (CH(ar)) 126.7 (*3); 128.1 (*6); 129.1 (*6); (C$_{ar}$) 140.4 (*3). MALDI-TOF: m/z=399.87 [M$^+$].

3 Preparation of Compound 1,4,7-triazacyclononane (Tacn)

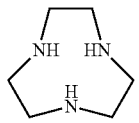
(3)

84.77 g of compound 2 (0.21 mol) are placed in 1 L of acetic acid with 9 g of Pd/C at 10% (8 mmol, 0.04 equivalent) under H$_2$. After consumption of 14.3 L of hydrogen (0.63 mol, 3 equivalents), the mix is filtered on celite and the solvent is evaporated. 52 mL of hydrochloric acid are added, followed by 250 mL of ethanol. The precipitate obtained is filtered and washed with 200 mL of diethyl ether. The compound 3 is obtained in the form of a white solid (25 g, yield=95%). $^1$H NMR (300 MHz, D$_2$O, 300 K) δ(ppm): 3.47 (s, 12H). $^{13}$C{$^1$H} NMR (75 MHz, D$_2$O, 300 K) δ(ppm): (CH$_2$) 42.4. MALDI-TOF: m/z=129.70 [M$^+$].

Example B: Preparation of Compound (1,4,7-triazacyclononane-2-yl)methanamine (6)

4 Preparation of the Reactional Intermediary 1,4,7-tribenzyl-1,4,7-triazacyclononane-2carbonitrile

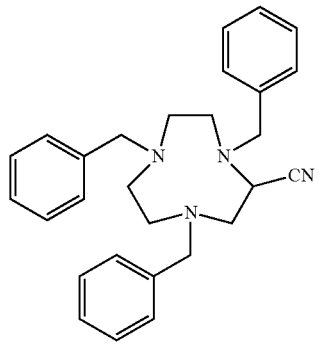
(4)

259.3 g of benzyl bromide (1.5 mol, 3 equivalents) are added drop by drop to a solution of 1 (64.3 g, 0.5 mol) and 278.8 g of K$_2$CO$_3$ (2.0 mol, 4 equivalents) in 1.1 L of acetonitrile at 10° C. The mix is stirred for 12 hours. 24.76 g of sodium cyanide (0.505 mol, 1 eq) are added carefully. The mix is stirred at ambient temperature for 4 days. After filtration on celite, the solvent is evaporated, 3 L of diethyl ether are added on the residual oil and insoluble impurities are eliminated by filtration. After evaporation of the solvent, the compound 4 is obtained in the form of a brown oil (137.2 g. yield=63%). $^1$H NMR (300 MHz. CDCl$_3$. 298 K) δ(ppm): 1.53-1.78 (m. 1H); 2.43-2.56 (m. 4H); 2.66-2.74 (m. 1H); 2.82-2.88 (m. 2H); 2.95-2.99 (m. 1H); 3.14-3.22 (m. 1H); 3.42-3.53 (m. 1H); 3.63-3.84 (m. 6H); 7.19-7.33 (m. 15H). $^{13}$C{$^1$H} NMR (75 MHz. CDCl$_3$. 298 K) δ (ppm): 54.7 (CH); 55.5; 56.4; 57.4; 58.8; 61.4; 62.1; 63.5; 65.9 (CH$_{2\alpha}$); 118.0 (CN); 126.8; 127.1; 127.7; 128.0; 128.1; 128.2; 128.3; 128.4; 128.6; 128.8; 129.0; 129.1 (*2); 129.2; 129.4 (CH$_{ar}$) 138.2; 139.3; 139.9 (C$_{ar}$). ESI-MS: m/z=398.24 [M-CN+2H]$^+$; 425.25 [M+H]$^+$. IR (cm$^{-1}$): 2250 (CN).

5 Preparation of the Reactional Intermediary (1,4,7-tribenzyl-1,4,7-triazacyclononane-2yl)methanamine

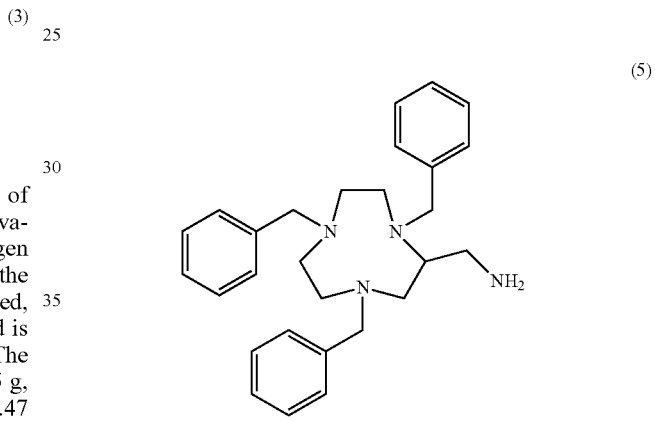
(5)

A solution of 4 (112.7 g, 0.27 mol) in 450 mL of THF is added very slowly at −78° C. under nitrogen to a suspension of 11.5 g of LiAlH$_4$ (0.32 mol, 1.2 eq) in 450 mL of THF. The mix is stirred for 12 h. 100 mL of water are added carefully on the mix. After evaporation of the solvent, the grey-green solid obtained is dissolved in 1 L of chloroform, the solution is filtered on celite to eliminate impurities. After evaporation of the solvent, the brown residual oil is placed in 200 mL of acetone and 200 mL of HCl at 37% are added slowly. The white precipitate is isolated by filtration and is recrystallised in water to give the protonated form of compound 2 (83.9 g, 0.20 mol). The compound is deprotonated by the addition of a solution of 16 M soda until a pH of 12 is reached. After extraction with chloroform (2*500 mL) and drying of the organic phase on MgSO$_4$, the solvent is evaporated. The compound 5 is obtained in the form of a yellow oil (45.3 g, yield=39%). $^1$H NMR (300 MHz, CDCl$_3$, 298 K) δ(ppm): 1.45 (m, 2H); 2.39-2.86 (m, 10H); 3.03-3.11 (m, 1H); 3.35-3.75 (m, 7H); 3.85 (bs, 1H); 7.24-7.44 (15H). $^{13}$C{$^1$H} NMR (75 MHz. CDCl$_3$. 298 K) δ (ppm): 42.5; 51.1; 52.8; 55.1; 55.6; 57.9; 58.2 (CH$_{2\alpha}$); 62.8 (CH); 63.5; 64.3 (CH$_{2\alpha}$) 126.7; 127.0; 127.1; 128.3 (*9); 128.8; 129.2; 129.5 (CH$_{ar}$); 140.2; 140.4; 141.2 (C$_{ar}$). ESI-MS: m/z=429.31 [M+H]$^+$. HMRS-ESI: calculated m/z for C$_{28}$H$_{36}$N$_4$+H=429.3012, obtained=429.3060.

6 Preparation of Compound (1,4,7-triazacyclononane-2-yl)methanamine

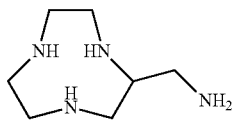

(6)

The compound 5 (5.0 g, 11.7 mol) is dissolved in a mix of acetic acid (29 mL), water (29 mL) and THF (98 mL). 500 mg of Pd/C at 10% (0.47 mmol, 0.04 equivalent) are added under $H_2$. After consumption of the expected hydrogen volume, palladium is eliminated by filtration on celite. After evaporation of the solvent, the residue is dissolved in ethanol (100 mL). 5 mL of hydrochloric acid at 37% are then added. After 1 hour, the precipitate formed is isolated by filtration and is then washed with 20 mL ethanol. The precipitate is recrystallised in water. The compound is deprotonated by addition of a solution of 16 M soda on the crystals until a pH of 12 is reached. After extraction with chloroform (2*500 mL), and drying of the organic phase on $MgSO_4$, the solvent is evaporated to obtain 6 in the form of a yellow oil (m=0.79 g, yield=44%). $^1$H NMR (300 MHz, $D_2O$, 300 K) δ (ppm): 2.98-3.58 (m, 13H). $^{13}C\{^1H\}$ NMR (75 MHz, $D_2O$, 300 K) δ(ppm): ($CH_2$) 40.9; 42.0; 42.9; 45.2; 46.2; 47.2; (CH) 50.6. MALDI-TOF: m/z=158.74 [M$^+$].

Example C: Preparation of Compound tert-butyl(tacn)methylcarbamate (8)

7 Preparation of the Reactional Intermediary tert-butyl (1,4,7-tribenzyl-1,4,7triazacyclononane-2-yl)methylcarbamate

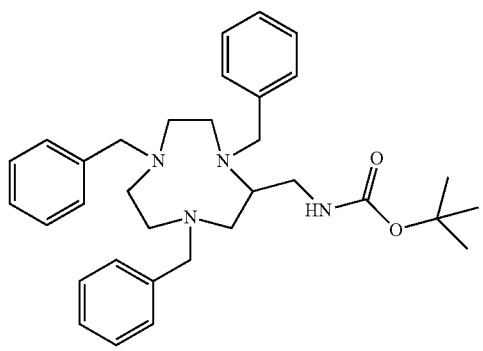

(7)

A solution of $Boc_2O$ (4.20 g, 19.2 mmol) in $CH_2Cl_2$ (100 mL) is slowly added to 5 (8.24 g, 19.2 mmol) in $CH_2Cl_2$ (150 mL). The solution is stirred at ambient temperature for 24 h. After evaporation of the solvent, oil is purified by chromatography on alumina (eluant: $CH_2Cl_2$) in order to obtain compound 7 in the form of a yellow oil (m=7.38 g, yield=73%). $^1$H NMR (300 MHz. $CDCl_3$, 298 K) δ(ppm): 1.42 (s, 9H. $CH_3$); 2.34-2.67 (m, 8H); 2.83-2.92 (m, 1H); 2.97-3.16 (m, 2H); 3.35-3.65 (m, 7H); 4.05 (m, 1H); 4.94 (m, 1H); 7.15-7.33 (m, 15H). $^{13}C\{^1H\}$ NMR (150 MHz, $CDCl_3$, 298 K) δ(ppm): 28.7 (*3) ($CH_3$); 40.7; 50.6; 53.2; 55.3; 56.2; 57.9; 58.1 ($CH_2$); 58.5 (CH); 63.8; 64.2 ($CH_2$); 79.0 (C); 126.8; 127.0; 127.2; 128.4 (*6); 129.0 (*2); 129.2 (*2); 129.5 (*2) ($CH_{ar}$); 140.1; 140.3; 140.7 ($C_{ar}$); 156.3 (C=O). ESI-MS: m/z=529.35 [M+H]$^+$. HMRS-ESI: m/z calculated for $C_{33}H_{44}N_4O_2$+H=529.3537, obtained=529.3528.

8 Preparation of Compound tert-butyl ((1,4,7-triazacyclononane-2-yl)methyl)carbamate

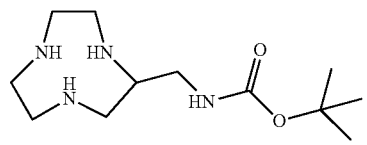

(8)

Compound 7 (3.33 g, 6.30 mmol) is dissolved in a mix of acetic acid (20 mL), water (20 mL) and THF (60 mL). 266 mg of Pd/C at 10% (0.25 mmol, 0.04 equivalent) are added under $H_2$. After consumption of the expected hydrogen volume, palladium is eliminated by filtration on celite. After evaporation of the solvent, the residue is dissolved in ethanol (100 mL). 5 mL of a 3 M hydrochloric acid solution are then added. After 1 hour, the precipitate formed is isolated by filtration and is then washed with 20 mL of ethanol and dried under a vacuum to give a white powder. The compound is deprotonated by the addition of a 3 M soda solution. After extraction with chloroform (2*50 mL), and drying of the organic phase on $MgSO_4$, the solvent is evaporated to obtain 8 in the form of a yellow oil (m=1.30 g, yield=80%). $^1$H NMR (300 MHz, $CDCl_3$, 298 K) δ(ppm): 1.39 (s, 9H, $CH_3$); 2.35-3.24 (m, 13H); 4.28-4.55 (m, 3H, NH); 5.83 (s, 1H, NHC=O), $^{13}C\{^1H\}$ NMR (150 MHz, $CDCl_3$, 298 K) δ(ppm): 28.6 (*3) ($CH_3$); 43.1; 44.0; 44.6; 45.6; 45.9 ($CH_2$); 46.8 (CH); 79.5 (C); 156.8 (C=O). ESI-MS: m/z=203.15 [M-$^t$Bu+H]$^+$; 259.15 [M+H]$^+$. HMRS-ESI: calculated m/z for $C_{12}H_{27}N_4O_2$=259.212; obtained=259.2116.

Example D: Preparation of Compound (2-(aminomethyl)-1,4,7-triazacyclononane-1,4,7-triyl)tris(methylene))tris(methylphosphinic acid) (10)

9 Preparation of the Reactional Intermediary tert-butyl ((1,4,7tris((ethoxy(methyl)phosphoryl)methyl)-1,4,7-triazacyclononane-2-yl)methyl)carbamate

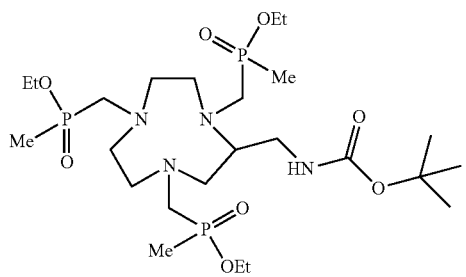

(9)

420 mg de 8 (1.12 mmol) and 818 mg of diethoxymethylphosphine (6.01 mmol) are placed in a tank under nitrogen bubbling for 5 minutes. The mix is then heated to 80° C. 189 mg of paraformaldehyde (6.01 mmol) are added and the mix is stirred for 2 h. After returning to ambient temperature, water is added (5 mL) and a 3M HCl solution is added until a pH of 5 is reached. The solution is washed twice with 30 mL of diethyl ether. A solution of 3M NaOH soda is slowly added until the pH is 13. The aqueous phase is washed with 2*50 mL of chloroform. The organic phase is dried on MgSO$_4$. After evaporation of the solvent, the residual oil is purified by Flash chromatography on silica (A: CH$_2$Cl$_2$, B: MeOH, B 0%→60%, rt=4.2 min) The compound 9 is obtained in the form of a yellow oil (m=360 mg, yield=58%). $^1$H NMR (300 MHz, CDCl$_3$, 298 K) δ(ppm): 1.30 (t, 9H, $^2$J=7 Hz, PCH$_3$); 1.41 (s, 9H, CH$_3$); 1.45-1.54 (m, 9H, PCH$_2$CH$_3$); 2.77-3.15 (m, 19H); 4.06 (m, 6H, PCH$_2$CH$_3$); 5.83 (s, 1H, NH).

10 Preparation of Compound (2-(aminomethyl)-1,4,7-triazacyclononane-1,4,7-triyl)tris(methylene))tris(methylphosphinic acid)

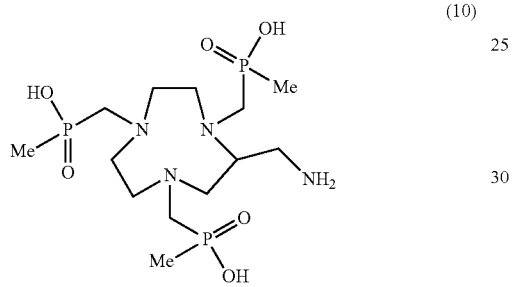

(10)

10 mL of a 37% HCl solution are added to 60 mg of compound 9 (0.10 mmol). The mix is heated to 90° C. for 2 days. After evaporation, the compound 10 (3 HCl) is isolated in the form of a white powder (m=54.4 mg, yield=100%). $^1$H NMR (500 MHz, D$_2$O, 298 K) δ(ppm): 1.37-1.49 (m, 9H), 2.82-3.60 (m, 19H). $^{31}$P{$^1$H} NMR (202 MHz, D$_2$O, 298 K) δ(ppm): 38.4; 45.2; 49.2. ESI-MS: m/z=435.17 [M+H]$^+$; 457.15 [M+Na]$^+$. HMRS-ESI: calculated for C$_{13}$H$_{33}$N$_4$O$_6$P$_3$+H: 435.1686; obtained 435.1696; calculated for C$_{13}$H$_{33}$N$_4$O$_6$P$_3$+Na 457.1505; obtained 457.1511.

Example E: Preparation of Compound ((2-(acetamidomethyl)-1,4,7-triazacyclononane-1,4,7-triyl)tris(methylene))tris(methylphosphinic acid) (11)

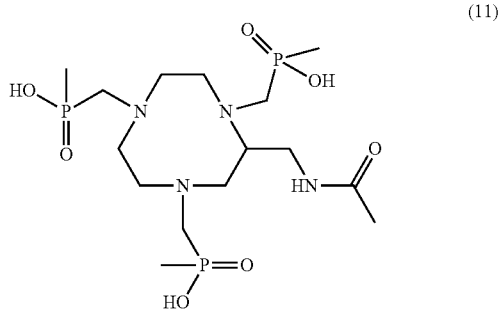 [SMILES: CC(=O)NCC1CN(CP(C)(=O)O)CCN(CP(C)(=O)O)CCN1CP(C)(=O)O]

(11)

An excess of acetic anhydride (100 µL) was added to 20 mg of compound 10 (0.041 mmol). At first our compound was not dissolved completely in acetic anhydride but after one night stirring at room temperature, a clear brown solution is obtained. Excess of acetic anhydride was removed by addition of 1 mL of water and evaporation. This was repeated twice and finally the solution in water was freeze-dried. The compound 11 was obtained as a light brown powder (m=14.5 mg, yield=70%). $^1$H NMR (300 MHz, D$_2$O, 300 K) δ (ppm): 1.50 (d, 9H, $^2$J=13.5 Hz, PCH$_3$), 2.02 (s, 3H, C=OCH$_3$), 2.95-3.96 (m, 19H). $^{31}$P{$^1$H} NMR (300 MHz, D$_2$O, 300 K) δ (ppm): 37.9, 39.3, 47.4. MALDI-TOF: m/z=477.00 [M+H]$^+$, 498.98 [M+Na]$^+$. HRMS-ESI: m/z=calculated for C$_{15}$H$_{35}$N$_4$O$_7$P$_3$+H$^-$: 477.1791, obtained 477.1778.

Example F: Preparation of 2,2',2''-(2-((bis(carboxymethyl)amino)methyl)-1,4,7-triazacyclononane-1,4,7-triyl)triacetic acid (13)

12 Preparation of the Reactional Intermediary tri-tert-butyl-2,2',2''-(2-((bis(2-(tert-butoxy)-2-oxoethyl)amino)methyl)-1,4,7-triazacyclononane-1,4,7-triyl) triacetate

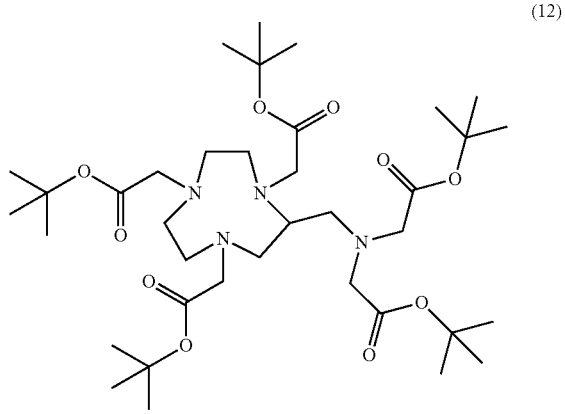 [SMILES: CC(C)(C)OC(=O)CN1CCN(CC(=O)OC(C)(C)C)CC(CN(CC(=O)OC(C)(C)C)CC(=O)OC(C)(C)C)N(CC(=O)OC(C)(C)C)CC1]

(12)

A solution of tertbutyl bromoacetate (4.66 g, 23.89 mmol) is added to a solution of 6 (756 mg, 4.79 mmol) and K$_2$CO$_3$ (6.61 g, 4.89 mmol) in 16 mL of acetonitrile. The mix is heated to 45° C. for 24 h. After returning to ambient temperature, the solution is filtered on celite and the solvent is evaporated. The residual oil is dissolved in ether and impurities are eliminated by filtration. The residue is purified by chromatography on alumina (eluant: CH$_2$Cl$_2$/MeOH 99:1), to give 12 in the form of a yellow oil (m=1.89 mg, yield=54%). $^1$H NMR (300 MHz, CDCl$_3$, 298 K) δ (ppm): 1.38-1.41 (m, 45H, CH$_3$); 2.43 (dd, 1H, J=13.2, 7.7 Hz); 2.60-3.11 (m, 11H); 3.19-3.45 (m, 10H); 4.02-4.13 (m, 1H). $^{13}$C{$^1$H} NMR (75 MHz, CDCl$_3$, 298K) δ (ppm): 28.4 (*15) (CH$_3$); 52.4; 53.6; 54.7; 55.3; 55.4; 55.7; 55.9; 56.0; 56.2; 57.0; 59.8; 61.1 (CH$_2$+CH); 80.4; 80.6; 80.7; 80.8 (*2) (C); 171.0 (*2); 171.7; 171.8; 172.3 (C=O). ESI-MS: m/z=729.5 [M+H]$^+$; 751.5 [M+Na]$^+$.

13 Preparation of 2,2',2''-(2-((bis(carboxymethyl)amino)methyl)-1,4,7-triazacyclononane-1,4,7-triyl)triacetic acid

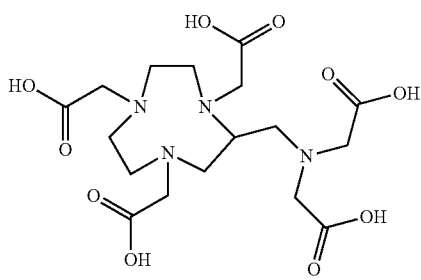

(13)

10 mL of a 37% hydrochloric acid solution are added to 50 mg of compound 12 (0.07 mmol). The mix is stirred for 1 hour at ambient temperature. After evaporation of the solvent, the precipitate obtained is washed with 40 mL of acetone. After filtration, the compound 13 is obtained in the form of a white solid (m=360 mg, yield=58%). ESI-MS: m/z=449.3 [M+H]$^+$; 471.2 [M+Na]+; 493.2 [M+2NaH]$^+$. HMRS-ESI: calculated m/z for $C_{17}H_{28}N_4O_{10}$+H 449.1878; obtained 449.1858.

Example G: Preparation of Compound 1,4,7-tris(pyridin-2-ylmethyl)-1,4,7-triazacyclononane (14)

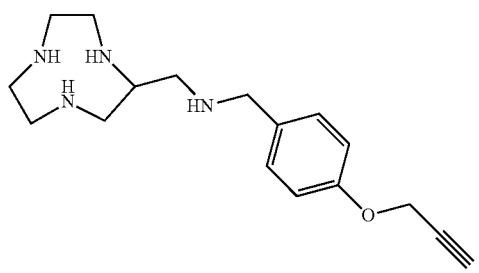

(14)

9.85 g of 2-(bromomethyl)pyridine bromohydrate (39.0 mmol, 3 eq) are slowly added at 10° C. to a solution of 1 (1.62 g, 13.0 mmol) and 45.5 g de $K_2CO_3$ in 90 mL of acetonitrile. The mix is stirred at ambient temperature for 24 h. After filtration on celite, the solvent is evaporated. The residual oil is dissolved in 200 mL of diethyl ether and the solution is stirred for 24 h. The precipitate is isolated by filtration, washed with 2*20 mL of diethyl ether and then dried under a vacuum to give 12.96 g of reactional intermediary. 5.0 g of this intermediary (10.3 mmol) are placed in 45 mL of ethanol and 3.9 g of $NaBH_4$ (103.0 mmol) are added at −10° C. After 12 h, the solvent is evaporated and 50 mL of diethyl ether are added on the residual oil Impurities are eliminated by filtration and the solvent is evaporated. The compound 14 is obtained in the form of an orange oil (m=1.62 g, yield=31%). $^1$H NMR (300 MHz, $CDCl_3$, 298 K) δ (ppm): 3.06 (s, 12H); 4.34 (s, 6H); 7.80-7.84 (m, 3H); 7.92-7.95 (m, 3H); 8.33-8.39 (m, 3H); 8.64-8.66 (m, 3H). $^{13}C\{^1H\}$ NMR (75 MHz, $CDCl_3$, 298K) δ (ppm): 49.3 (*6); 56.3 (*3); 126.4 (*3); 127.3 (*3); 143.5 (*3); 145.6 (*3); 150.3 (*3). ESI-MS: m/z=403.26 [M+H]$^+$.

Example H: Preparation of Compound N-((1,4,7-triazacyclononane-2-yl)methyl)-1-(4-(prop-2-yN-1-yloxy)phenyl) methanamine (16)

15 Preparation of the Reactional Intermediary N-((1,4,7-triazacyclononane-2-yl)methyl)1-(4-(prop-2-yN-1-yloxy)phenyl) methanamine (15)

101 mg of 3-(prop-2-ynyloxy)benzaldehyde (0.63 mmol) are added to a solution of 6 (100 mg, 0.63 mmol) in 25 mL of ethanol, and the mix is stirred at ambient temperature for 48 h. The solvent is then evaporated and 25 mL of diethylether are added on the residual oil. After 12 h, the impurities are eliminated by filtration on celite. The solvent is evaporated, oil is placed in 10 mL of ethanol and 250 mg of $NaBH_4$ (6.7 mmol) are added at 0° C. The mix is stirred at ambient temperature for 24 h. The solvent is evaporated, 25 mL of dichloromethane are added on the residual solid and impurities are eliminated by filtration. The solution is washed with a 3M soda solution (10 mL), dried on $MgSO_4$ and the solvent is evaporated. The compound 15 is obtained in the form of a white solid (m=135 mg, yield=68%). $^1$H NMR (300 MHz, $CDCl_3$, 298 K) δ(ppm): 1.10-1.60 (m, 3H); 2.30-2.90 (m, 15H); 3.65 (s, 2H); 4.61 (d, 2H, $^4$J=2.3 Hz); 6.86 (d, 2H, $^3$J=8.7 Hz); 7.18 (d, 2H, $^3$J=8.7 Hz). $^{13}C\{^1H\}$ NMR (75 MHz, $CDCl_3$, 298K) δ (ppm): 46.0; 46.4; 47.0; 47.2; 47.3; 49.9; 53.6; 55.6; 55.9; 75.6; 78.8; 114.8 (*2); 129.3 (*2); 130.1; 156.6. ESI-MS: m/z=303.22 [M+H]$^+$.

16 Preparation of Compound tri-tert-butyl-2,2',2''-(2-(((4-(prop-2-yn-1-yloxy)benzyl)amino)methyl)-1,4,7-triazacyclononane-1,4,7-triyl)triacetate

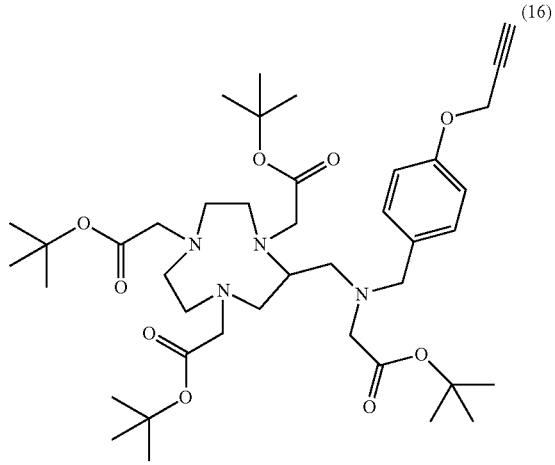

(16)

A solution of tertbutyl bromoacetate (341 mg, 1.75 mmol) is added to a solution of 15 (135 mg, 0.44 mmol) and $K_2CO_3$ (484 mg, 3.50 mmol) in acetonitrile (15 mL). The mix is heated to 45° C. for 24 h. After returning to ambient temperature, the solution is filtered on celite. The solvent is evaporated, 50 mL of diethyl ether are added on the residual oil Impurities are eliminated by filtration and the solvent is once again evaporated. Oil is purified by chromatography on alumina (eluant: $CH_2Cl_2$/MeOH 99:1). The compound 16 is obtained in the form of a yellow oil (m=100 mg, yield=30%). $^1$H NMR (300 MHz, $CDCl_3$, 298 K) δ(ppm): 1.36-1.42 (m, 36H); 2.49 (t, 1H, $^2J$=2.49 Hz); 2.50-3.77 (m, 23H); 4.61 (d, 2H, $^4J$=2.3 Hz); 6.83 (d, 2H, $^3J$=8.2 Hz); 7.18 (d, 2H, $^3J$=8.2 Hz). ESI-MS: m/z=759.50 [M+H]$^+$; 771.57 [M+Na]$^+$.

Example I: Preparation of Compound (1,4,7-triaza-cyclononane-2-yl)-boron dipyromethene Also Called (1,4,7-triazacyclononane-2-yl)-BODIPY (17)

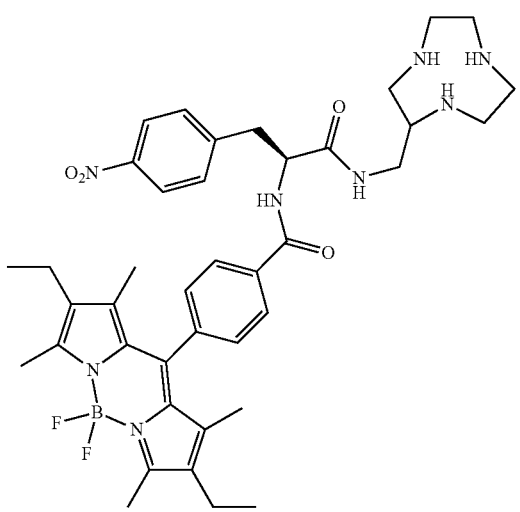

(17)

195 mg of 4,4-difluoro-8-(4-((1-carboxy-2-(4-nitrophenyl)ethyl)carbamoyl)phenyl) 1,3,5,7-tetramethyl-2,6-diethyl-4-bora-3a,4a-diaza-s-indacene (0.32 mmol), 42 mg of hydroxybenzotriazole (HOBt) (0.32 mmol) and 60 mg of 1-ethyl-3-(3-dimethylaminopropyl)carbodiimide (EDCI) (0.32 mmol) are successively added to a solution of 6 (50 mg, 0.32 mmol) in 10 mL of DMF. The mixed is stirred at ambient temperature and the reaction is followed by CCM ($CH_2Cl_2$/MeOH/$NH_4OH$ 10:85:5). The solvent is then evaporated. The red oil is dissolved in 20 mL of dichloromethane and washed three times with 10 mL of water. The organic phase is isolated and then dried on $MgSO_4$. The red oil is purified by chromatography on silica gel (EtOH/$NH_4OH$ 80:20). The oil obtained is then dissolved in a $CH_2Cl_2$/hexane mix, the precipitate formed is isolated by filtration. The compound 17 is obtained in the form of a red solid (m=180 mg, yield=74%). $^1$H NMR (300 MHz, MeOD, 300 K) δ (ppm): 0.94 (t, 6H, $^3J$=7.5 Hz), 1.24 (s, 6H); 2.29 (q, 4H, $^3J$=7.5 Hz); 2.38 (s, 6H); 2.48-2.60 (m, 1H); 2.61-3.22 (m, 12H); 3.27-3.40 (m, 2H); 4.83-4.90 (m, 1H); 7.39 (d, 2H, $^3J$=8.1 Hz); 7.54 (d, 2H, $^3J$=8.5 Hz); 7.93 (d, 2H, $^3J$=8.5 Hz); 8.11 (d, 2H, $^3J$=8.1 Hz).

Example J: Preparation of Compound di-tert-butyl hexahydroimidazo[1,2-a]pyrazine1,7-dicarboxylate (18)

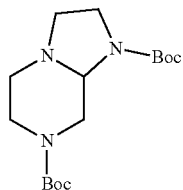

(18)

A solution of $Boc_2O$ (5.79 g, 26.6 mol) diluted in 30 mL of dichloromethane is added drop by drop to solution 1 (1.69 g, 13.3 mmol) in dichloromethane (30 mL). The mixed is stirred at ambient temperature for 24 h. After evaporation of the solvent, oil is dissolved in 50 mL of diethyl ether and the impurities are eliminated by filtration. The compound 18 is isolated in the form of a light brown solid (m=3.98 g, yield=91%). $^1$H NMR (300 MHz, $CDCl_3$, 298 K) δ(ppm): 3.32-3.39 (m, 18H); 4.37-4.67 (m, 2H); 4.73-5.98 (m, 8H); 6.44 (m, 1H). ESI-MS: m/z=328.15 [M+H]$^+$.

Example K: Preparation of Compound 4-benzyl-1,7-bis(tert-butoxycarbonyl) octahydro-1H-imidazo[1,2-a]pyrazin-4-ium bromide (19)

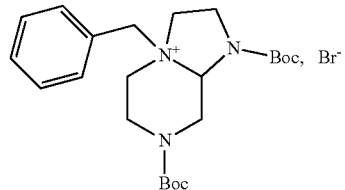

(19)

A solution of benzyl bromide (742 mg, 4.3 mmol) diluted in acetonitrile (5 mL) is added at 0° C. to a solution of 18 (1.45 g, 4.34 mmol) in acetonitrile (10 mL). The mix is stirred at ambient temperature for 24 h. After evaporation of the solvent, oil is dissolved in 20 mL of diethyl ether, the precipitate is filtered, washed with 2*10 mL of diethyl ether and dried under a vacuum. The compound 19 is obtained in the form of a beige solid (m=1.31 g, yield=61%). $^1$H NMR (500 MHz, $CDCl_3$, 320 K) δ(ppm): 11.35 (s, 9H); 1.51 (s, 9H); 3.58-3.66 (m, 2H); 3.70-3.78 (m, 1H); 3.81-3.93 (m, 3H); 4.13-4.20 (m, 1H); 4.46 (m, 1H); 4.56-4.65 (m, 1H); 4.75 (d, 1H, $^2J$=12.3 Hz); 4.83 (m, 1H); 5.19 (m, 1H); 5.46 (d, 1H, $^2J$=12.3 Hz); 7.45-7.51 (m, 3H); 7.59 (d, 2H, $^3J$=7.1 Hz). ESI-MS: m/z=418.27 [M-Br]$^+$.

Example L: Preparation of Compound 4-benzyloctahydro-1H-imidazo[1,2-a]pyrazin-4-ium bromide (20)

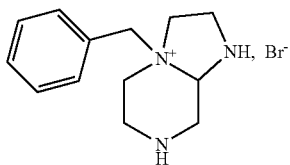
(20)

0.7 mL of a solution of 1M HCl are added very slowly to 19 (0.34 mg, 0.7 mmol). The solution is stirred for 1 h at ambient temperature. After evaporation of the solvent, compound 20 is obtained in the form of a white solid (m=0.07 mg, yield=36%). $^1$H NMR (300 MHz, CDCl$_3$, 298 K) δ(ppm): 3.09-3.11 (m, 2H); 3.34-3.48 (m, 8H); 4.37 (s, 2H); 5.30-5.34 (m, 1H); 7.52 (m, 5H). ESI-MS: m/z=218.16 [M-Br]$^+$.

Example M: Preparation of Compound 1,7-bis(tert-butoxycarbonyl)-4-methyloctahydro-1H-imidazo[1,2-a]pyrazin-4-ium iodide (21)

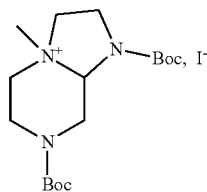
(21)

A solution of iodomethane (0.92 mg, 6.5 mmol) in acetonitrile (5 mL) is added drop by drop at 0° C. to a solution of 18 (2.12 g, 6.5 mmol) in acetonitrile (10 mL). The mix is stirred for 24 hours at ambient temperature. After evaporation of the solvent, the oil is dissolved in 30 mL of diethyl ether, the precipitate is filtered and washed with 2*10 mL of diethyl ether and dried under a vacuum. The compound 21 is obtained in the form of a yellow solid (m=1.78 g, yield=59%). $^1$H NMR (300 MHz, CDCl$_3$, 298 K) δ(ppm): 1.40-1.48 (m, 21H); 3.70-4.74 (m, 10H); 5.0 (m, 1H). ESI-MS: m/z=230.12 [M-I-2$^t$Bu+2H]$^+$, 286.19 [M-I-$^t$Bu+H]$^+$; 342.25 [M-I]$^+$.

Example N: Preparation of Compound (1,4,7-triazacyclononan-1-yl) ethanamine (24)

22 Preparation of the Reactional Intermediary 2-(hexahydroimidazo[1,2-a]pyrazin7(1H)-yl)ethanamine

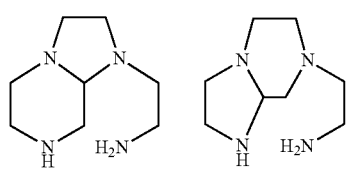
(22)

A solution of chloroacetaldehyde (50% in water, 2.36 g, 15 mmol) is added to a solution of triethylenetetraamine (3 g, 15 mmol) in 70 mL of acetonitrile at ambient temperature. The mixed is stirred for 5 h. After evaporation of the solvent, the two isomers 22 and 22' are obtained in the form of a yellow oil and will be used without additional purification (m=2.55 g, yield=100%). $^{13}$C{$^1$H} NMR (75 MHz, CDCl$_3$, 300 K) δ(ppm): (CH$_2$) 38.8; 40.8; 41.7; 43.6; 45.0; 48.7; 49.3; 49.4; 49.9; 51.0; 52.0; 52.1; 52.4; 52.6; (CH) 75.8; 81.7. MALDI-TOF: m/z=170.71 [M$^+$].

23 Preparation of the Reactional Intermediary N,N-dibenzyl-2-(4,7-dibenzyl-1,4,7-triazacyclononane-1-yl)ethanamine

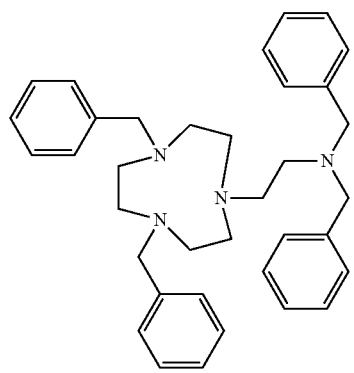
(23)

45.55 g of benzyl bromide (0.27 mol, 4 equivalents) are slowly added to a solution of 22 and 22' (11.32 g, 66 mmol) and 37.3 g of potassium carbonate (0.27 mol, 4 equivalents) in 250 mL of acetonitrile. The mix is stirred at ambient temperature for 24 h. After filtration on celite, the solvent is evaporated, oil is dissolved in 250 mL of ethanol and 2.5 g of sodium borohydride (66 mmol, 1 equivalent) are added at 0° C. After 12 h, the solvent is evaporated and 150 mL of chloroform are added. Insoluble impurities are eliminated by filtration. After evaporation of the solvent, oil is purified by chromatography on alumina (solvent: CH$_2$Cl$_2$). After evaporation of the solvent, 500 mL of pentane are added on the residual oil, the solution is filtered and the solvent is evaporated. The compound 23 is obtained in the form of a yellow oil (m=16 g, 30 mmol, yield=45%). $^1$H NMR (300 MHz, CDCl$_3$, 300 K) δ(ppm): 2.49-2.87 (m, 16H); 3.47 (s, 2H); 3.56 (s, 4H); 3.64 (s, 2H); 7.22-7.41 (m, 20H). $^{13}$C{$^1$H} NMR (75 MHz, CDCl$_3$, 300 K) δ(ppm): (CH$_2$) 51.4; 52.2; 52.3; 52.3; 55.4; 55.8; 56.3; 58.8 (*2); 58.9; 59.3; 63.2; (CH$_{ar}$) 126.8 (*4); 128.1 (*8); 128.7 (*8); (C$_{ar}$) 139.8 (*4). MALDI-TOF: m/z=533.06 [M$^+$].

24 Preparation of Compound (1,4,7-triazacyclononane-1-yl)ethanamine

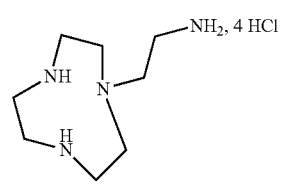
(24)

12.37 g of 23 (23 mmol) are placed in 130 mL of acetic acid with 1 g of Pd/C at 10% (0.04 equivalent, 1 mmol) under $H_2$. After consumption of 2.06 L of hydrogen (0.92 mol, 4 equivalents), palladium is eliminated by filtration and the solvent is evaporated. 7.7 mL of 37% HCl is added to the residual oil, then 50 mL of ethanol, forming a white precipitate. After filtration, the compound 24 is obtained in the form of a white solid (m=7.3 g, 23 mmol, yield=100%). $^1$H NMR (300 MHz, $D_2O$, 300 K) δ(ppm): 3.33-3.57 (m, 16H). $^{13}C\{^1H\}$ NMR (75 MHz, $D_2O$, 300 K) δ(ppm): ($CH_2$) 35.3 (*2); 43.3 (*2); 43.3; 44.6 (*2); 51.7. MALDI-TOF: m/z=172.41 [M$^+$].

Example O: Preparation of 2,2',2"-(2-(aminomethyl)-1,4,7-triazacyclononane-1,4,7-triyl)triacetic acid (26)

25 Preparation of the Reactional Intermediary tri-tert-butyl 2,2',2"-(2-(((tert-butoxycarbonyl)amino)methyl)-1,4,7-triazacyclononane-1,4,7-triyl)triacetate (25)

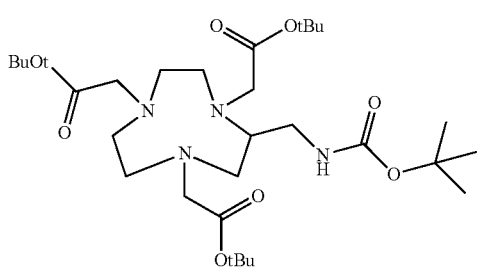

A solution of compound 8 (471.1 mg, 1.84 mmol) in dimethylformamide (9.2 mL) was heated at 40° C. Tert-butylbromoacetate (0.803 mL, 5.51 mmol) and potassium carbonate (1.78 g, 12.9 mmol) were added to this solution and the reaction mixture was stirred overnight. The suspension was filtered on a celite bed and the filter-cake was washed with chloroform. After evaporation of the solvents in vacuo, the crude was purified by flash chromatography on silica gel (eluent: $CH_2Cl_2/CH_3OH$ 94:6) and inverse phase flash chromatography (eluent: {HCOOH/$H_2O$ 0.01M}/$CH_3CN$ 60:40). 25 was obtained as a light yellow oil (m=50.5 mg, yield=5%). $^1$H NMR (600 MHz, $CDCl_3$, 325 K) δ(ppm): 1.39, 1.40, 1.43, 1.44 (4 s, 36H, $CH_3$), 2.64-3.26 (m, 12H), 3.27-3.38 (m, 2H), 3.43 (d, 1H, $^2J$=17.6 Hz), 3.60 (d, 1H, $^2J$=17.6 Hz), 3.68 (d, 1H, $^2J$=17.6 Hz), 3.70 (d, 1H, $^2J$=17.6 Hz), 3.79 (d, 1H, $^2J$=17.6 Hz), 6.03 (bs, 1H, NHBoc). $^{13}C\{^1H\}$ NMR (75 MHz, $CDCl_3$, 298 K) δ(ppm): 28.1, 28.2, 28.3, 28.6 ($CH_3$), 39.3 ($CH_2NH$) 51.6, 53.3, 55.9, 56.8, 79.8, 82.1, 82.5, 83.1 ($C_q^tBu$), 156.7 (CONHO$^t$Bu), 167.4, 168.8, 171.3. ESI-MS: m/z=601.46 [M+H]$^+$. HRMS-ESI: m/z=calculated for $C_{30}H_{56}N_4O_8$+H: 601.4171 obtained 601.4145.

26 Preparation of Preparation of 2,2',2"-(2-(aminomethyl)-1,4,7-triazacyclononane-1,4,7-triyl)triacetic acid (26)

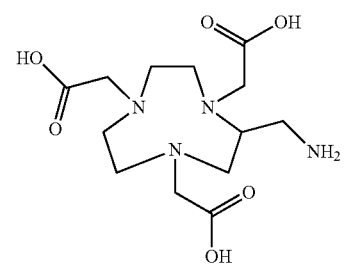

Trifluoroacetic acid (1 mL) was added to a stirred solution of compound 25 (49.5 mg, 0.08 mmol) in dichloromethane (2 mL). The resulting reaction mixture was stirred overnight at room temperature before it was concentrated in vacuo. Compound 26 was obtained as a light yellow oil and was directly used without purification. $^1$H NMR (300 MHz, $D_2O$, 295 K) δ(ppm): 2.36-3.19 (m, 7H), 3.20-3.27 (m, 2H), 3.29-3.44 (m, 3H), 3.53-3.88 (m, 4H), 3.92-4.25 (m, 3H). ESI-MS: m/z=333.27 [M+H]$^+$.

Example P: Preparation of 2,2',2"-(2-((2-(4-isothiocyanatophenyl)acetamido)methyl)-1,4,7-triazacyclononane-1,4,7-triyl)triacetic acid (28)

27 Preparation of the Reactional Intermediary 2,2', 2"-(2-((2-(4-nitrophenyl)acetamido)methyl)-1,4,7-triazacyclononane-1,4,7-triyl)triacetic acid (27)

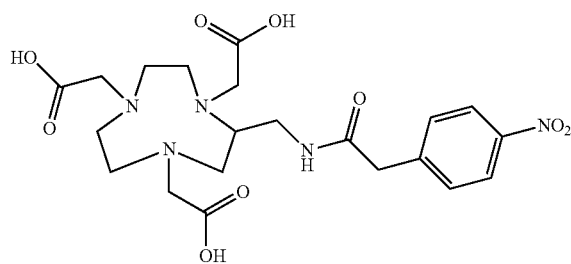

N,N-Diisopropylethylamine was added dropwise to a stirred solution of 26 (0.082 mmol) in water (2 mL) until pH reached 9.4. The solution is yellowish. Quickly, N-succinimidyl-4-nitrophenylacetate (22.8 mg, 0.082 mmol) dissolved in acetonitrile (1 mL) was added and the reaction mixture turned immediately red. The solution is stirred for 2 hours and the solvents are evaporated in vacuo and freeze-dried. To remove some impurities the crude compound was diluted in water (5 mL) and chloroform (5 mL). The aqueous phase was washed with chloroform (2×5 mL) and the organic phase was extracted with water (5 mL). The combined aqueous layers were freeze-dried and 27 was obtained as a light brown powder and was directly used without purification. ESI-MS: m/z=494.06 [M−H]$^-$.

28 Preparation of the Reactional Intermediary 2,2',2"-(2-((2-(4-aminophenyl)acetamido)methyl)-1,4,7-triazacyclononane-1,4,7-triyl)triacetic acid (28)

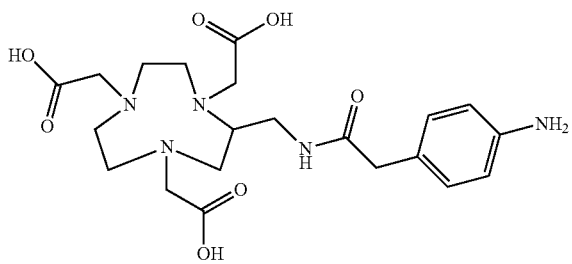

(28)

Compound 27 (0.082 mmol) was dissolved in water (1.4 mL) and 3.5 mg of 10% Pd/C (3·10$^{-3}$ mmol, 0.04 equivalent) was added under H$_2$. The solution was stirred vigorously and after consumption of hydrogen, the mixture was filtered on a celite bed to remove palladium and the filter-cake was washed with water. The crude compound was freeze-dried and 28 was obtained as a light yellow powder and was directly used without purification. ESI-MS: m/z=464.09 [M−H]$^−$.

29 Preparation of 2,2',2"-(2-((2-(4-isothiocyanatophenyl)acetamido)methyl)-1,4,7-triazacyclononane-1,4,7-triyl)triacetic acid (29)

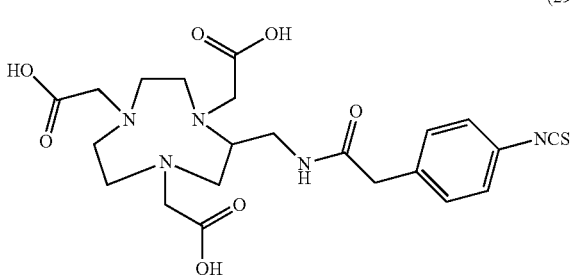

(29)

Compound 28 (0.082 mmol) was dissolved in water (1.4 mL) and the solution was stirred vigorously. In a test tube thiophosgene (37.8 μL, 0.49 mmol) was dissolved in dichloromethane (0.45 mL) and the mixture was added to the previous solution rapidly. The reaction was stirred for 3 hours. The aqueous phase was isolated and washed with chloroform. The crude compound was purified by semi-preparative HPLC column (System 3, t$_r$=32.3 min) to obtained 29 as a light brown powder (5.0 mg, 0.010 mmol). The overall yield of the last four reactions is 12%. $^1$H NMR (300 MHz, D$_2$O, 295 K) δ(ppm): 2.61-2.75 (m, 1H), 2.78-2.91 (m, 1H), 2.94-3.50 (m, 12H), 3.58 (s, 2H, PhCH$_2$CO), 3.65-4.05 (m, 5H), 7.31 (s, 4H, CH$_{ar}$). ESI-MS: m/z=507.98 [M+H]$^+$. HRMS-ESI: m/z=calculated for C$_{22}$H$_{29}$N$_5$O$_7$S+H: 508.1861 obtained 508.1881. m/z=calculated for C$_{22}$H$_{29}$N$_5$O$_7$S+Na: 530.1680 obtained 530.1687. Elemental analysis for C$_{22}$H$_{29}$N$_5$O$_7$S+CHCl$_3$+2H$_2$O: Calculated: C (41.67%), H (5.17%), N (10.56%), S (4.84%). Obtained: C (41.32%), H (5.23%), N (10.75%), S (3.06%).

Example Q: ((2-((2-(4-isothiocyanatophenyl)acetamido)methyl)-1,4,7-triazacyclononane-1,4,7-triyl)tris(methylene))tris(methylphosphinic acid) (30)

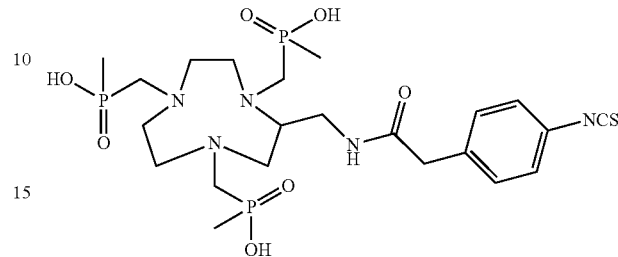

(30)

Compound 30 was obtained in three steps reaction starting from compound 10 by following the same procedure described for the preparation of compound 29 (Example P above).

The invention claimed is:
1. A compound of general formula (V')

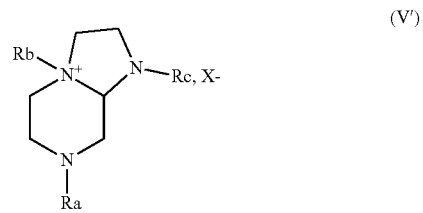

(V')

wherein
X represents a radical selected from the group consisting of bromo, iodo, and chloro radicals;
Ra, Rb and Rc may be identical or different and each represents
a hydrogen atom, or
a —(CH$_2$)$_n$—R' group wherein n and R' are defined as:
(i) n is equal to 0, 1, 2, 3, 4, 5, or 6 and R' represents a saturated or unsaturated, branched or unbranched, substituted or unsubstituted aliphatic group, comprising 1 to 12 carbon atoms, wherein when the aliphatic group is substituted, it is by one or several substituents, selected from the group consisting of halo, hydroxyl, oxo, nitro, amido, carboxy, amino, cyano, haloalkoxy, and haloalkyl;
(ii) n is equal to 0 and R' represents —CH(COOR'$_4$)(CH$_2$)$_{m4}$COOR'$_5$ wherein m$_4$ is equal to 1, 2 or 3 and R'$_4$, R'$_5$ are identical or different and each represent a hydrogen atom or a group selected from the groups consisting of alkyl, benzyl, paranitrobenzyl, pentafluorobenzyl, N-hydroxysuccinimide (NHS), and sulfo-NHS;
(iii) n is equal to 0, 1, 2, 3, 4, 5, or 6 and R' represents an unsubstituted benzyl group or a benzyl group substituted in the meso and/or meta and/or para and/or ortho position by one or several radicals selected from the group consisting of cyano, nitro, amino, halo, alkoxy, and hydroxy radicals;
(iv) n is equal to 0, 1, 2, 3, 4, 5, or 6 and R' represents an unsubstituted methyl pyridine group or a methyl pyridine group substituted by one or several groups selected from the group consisting of cyano, nitro, amino, halo, alkoxy, and hydroxyl;

(v) n is equal to 0, 1, 2, 3, 4, 5, or 6 and R' represents an aromatic group selected from the group consisting of phenyl, biphenyl, 1-naphthyl, the 2-naphthyl, anthracenyl, pyrenyl, tetrahydronaphthyl, indanyl, binaphthyl, terpyridinyl, bipyridinyl, guanine, phenantroline, hydroxyquinoline and quinoline;

(vi) n is equal to 0, 1, 2, 3, 4, 5, or 6 and R' represents a SH group;

(vii) n is equal to 0, 1, 2, 3, 4, 5, or 6 and R' represents a —C(=O)—OR'$_1$ group wherein R'$_1$ represents a hydrogen atom or a saturated or unsaturated, branched or unbranched, substituted or unsubstituted aliphatic group, comprising 1 to 12 carbon atoms wherein when the aliphatic group is substituted, it is by one or several substituents, selected from the group consisting of halo, hydroxyl, oxo, nitro, amido, carboxy, amino, cyano, haloalkoxy, haloalkyl, and aryl;

(viii) n is equal to 0, 1, 2, 3, 4, 5, or 6 and R' represents a —(CH$_2$)$_2$—OR'$_1$ group wherein R'$_1$ is as defined above;

(ix) n is equal to 0, 1, 2, 3, 4, 5, or 6 and R' represents a —C(=O)—NHR'$_1$ group wherein R'$_1$ is as defined above;

(x) n is equal to 0, 1, 2, 3, 4, 5, or 6 and R' represents a —C(=O)—SR'$_1$ group wherein R'$_1$ is as defined above;

(xi) n is equal to 0, 1, 2, 3, 4, 5, or 6 and R' represents a —P(=O)—R'$_2$R'$_3$ group wherein R'$_2$ and R'$_3$ may be identical or different and each represents a —(CH$_2$)$_{m1}$—R''$_1$ group wherein m$_1$ is equal to 0, 1, 2, 3, 4, 5 or 6, and R''$_1$ represents a saturated or unsaturated aliphatic chain, optionally interrupted by one or several oxygen, nitrogen or sulphur atoms;

with the condition that Ra, Rb and Rc are not simultaneously three methyl groups.

2. The compound of general formula (V') according to claim 1, wherein Ra and Rc both represent —(C=O)OtBu groups and Rb represents alkyl or benzyl groups.

3. The compound of general formula (V') according to claim 1, selected from the group consisting of:
4-benzyl-1,7-bis(tert-butoxycarbonyl)octahydro-1H-imidazo[1,2-a]pyrazin-4-ium bromide;
4-benzyloctahydro-1H-imidazo[1,2-a]pyrazin-4-ium bromide; and
1,7-bis(tert-butoxycarbonyl)-4-methyloctahydro-1H-imidazo[1,2-a]pyrazin-4-ium iodide.

4. A method for preparation of a compound of formula (V)

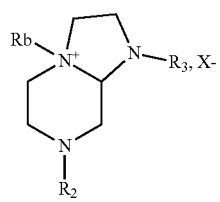

(V)

wherein
X represents a radical selected from the group consisting of bromo, iodo and chloro radical;

R$_1$ represents a (CH$_2$)$_p$—B radical wherein
p is equal to 1, 2, 3 or 4;
B represents
a hydrogen atom;
an unsubstituted phenyl radical or a phenyl radical substituted in the meta and/or para and/or ortho position by one or several radicals selected from the group consisting of cyano, nitro, amino, halo, alkoxy, and hydroxy radicals;
an unsubstituted pyridine radical or a pyridine radical substituted by one or several radicals selected from the group consisting of cyano, nitro, amino, halo, alkoxy, and hydroxy radicals;

R$_2$ represents R$_1$, R$_2$'', R$_2$'' modified by reaction with R$_1$—X or a Boc group,
where R$_2$'' represents a hydrogen atom or an aliphatic or aromatic group, optionally substituted by one or several radicals selected from the group consisting of cyano, nitro, amino, halo, alkoxy, and hydroxy radicals;

R$_3$ represents R$_1$, R$_3$'', R$_3$'' modified by reaction with R$_1$—X or a Boc group,
where R$_3$'' represents a hydrogen atom or an aliphatic or aromatic group, optionally substituted by one or several radicals selected from the group consisting of cyano, nitro, amino, halo, alkoxy, and hydroxy radicals;

said method comprising the following successive reaction steps (a) and (b):
a step (a) during which a compound of formula (II)

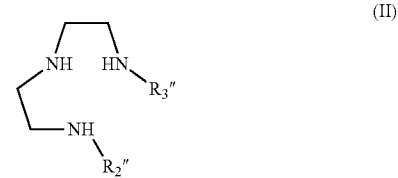

(II)

wherein R$_2$'' and R$_3$'' are as defined above;
reacts selectively with a compound of formula (III)

(III)

to form a compound of formula (IV)

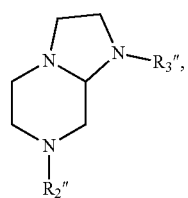

(IV)

step (a) being optionally followed, when R$_2$'' and R$_3$'' are each H, by an intermediate step (a'), wherein the compound (IV) is put in the presence of Boc$_2$O to form compound (IV')

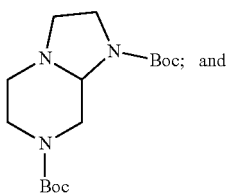

a step (b) during which the compound of formula (IV) or (IV') obtained, respectively, in step (a) or step (a'), reacts with R1-X to form the compound of formula (V).

5. A method for preparation of a compound of formula (V')

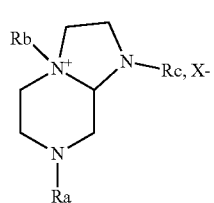

wherein
X represents a radical selected from the group consisting of bromo, iodo and chloro radicals;
Ra, Rb and Rc may be identical or different and each represents
a hydrogen atom, or
a —$(CH_2)_n$—R' group wherein n and R' are defined as
n is equal to 0, 1, 2, 3, 4, 5, or 6 and R' represents a saturated or unsaturated, branched or unbranched, substituted or unsubstituted aliphatic group, comprising 1 to 12 carbon atoms, wherein when the aliphatic group is substituted, it is by one or several substituents, selected from the group consisting of halo, hydroxyl, oxo, nitro, amido, carboxy, amino, cyano, haloalkoxy, and haloalkyl;
n is equal to 0 and R' represents —CH(COOR'$_4$)(CH$_2$)$_{m4}$COOR'$_5$ wherein m$_4$ is equal to 1, 2 or 3 and R'$_4$, R'$_5$ are identical or different and each represent a hydrogen atom or a group selected from the group consisting of alkyl, benzyl, paranitrobenzyl, pentafluorobenzyl, N-hydroxysuccinimide (NHS), and sulfo-NHS;
n is equal to 0, 1, 2, 3, 4, 5, or 6 and R' represents an unsubstituted benzyl group or a benzyl group substituted in the meso and/or meta and/or para and/or ortho position by one or several radicals selected from the group consisting of cyano, nitro, amino, halo, alkoxy, and hydroxy;
n is equal to 0, 1, 2, 3, 4, 5, or 6 and R' represents an unsubstituted methyl pyridine group or a methyl pyridine group substituted by one or several groups selected from the group consisting of cyano, nitro, amino, halo, alkoxy, and hydroxy;
n is equal to 0, 1, 2, 3, 4, 5, or 6 and R' represents an aromatic group selected from the group consisting of phenyl, biphenyl, 1-naphthyl, the 2-naphthyl, anthracenyl, pyrenyl, tetrahydronaphthyl, indanyl, binaphthyl, terpyridinyl, bipyridinyl, guanine, phenantroline, hydroxyquinoline and quinoline;
n is equal to 0, 1, 2, 3, 4, 5, or 6 and R' represents a SH group;
n is equal to 0, 1, 2, 3, 4, 5, or 6 and R' represents a —C(=O)—OR'$_1$ group wherein R'$_1$ represents a hydrogen atom or a saturated or unsaturated, branched or unbranched, substituted or unsubstituted aliphatic group, comprising 1 to 12 carbon atoms, wherein when the aliphatic group is substituted, it is by one or several substituents, selected from the group consisting of halo, hydroxyl, oxo, nitro, amido, carboxy, amino, cyano, haloalkoxy, haloalkyl, and aryl;
n is equal to 0, 1, 2, 3, 4, 5, or 6 and R' represents a —(CH$_2$)$_2$—OR'$_1$ group wherein R'$_1$ is as defined above;
n is equal to 0, 1, 2, 3, 4, 5, or 6 and R' represents a —C(=O)—NHR'$_1$ group wherein R'$_1$ is as defined above;
n is equal to 0, 1, 2, 3, 4, 5, or 6 and R' represents a —C(=O)—SR'$_1$ group wherein R'$_1$ is as defined above;
n is equal to 0, 1, 2, 3, 4, 5, or 6 and R' represents a —P(=O)—R'$_2$R'$_3$ group wherein R'$_2$ and R'$_3$ may be identical or different and each represents a —(CH$_2$)$_{m1}$—R''$_1$ group wherein m$_1$ is equal to 0, 1, 2, 3, 4, 5 or 6 and R''$_1$ represents a saturated or unsaturated aliphatic chain, or a saturated or unsaturated aliphatic chain interrupted by one or several oxygen, nitrogen or sulphur atoms,
said method comprising:
the method of preparation of a compound of formula (V) according to claim 4, wherein {R$_2$, R$_3$} represents {Boc, Boc};
one or more of a step (c) of deprotecting the compound of formula (V) in an acid medium; and
one or several steps (d) of chemically modifying the deprotected compound of formula (V) from step (c) to obtain the compound of formula (V').

6. The method of claim 5 wherein R''$_1$ represents (i) a —(CH$_2$)$_{m2}$—OR'$_1$ group wherein m$_2$ is equal to 0, 1, 2, 3, 4, 5 or 6, (ii) a —(CH$_2$)$_{m3}$—C(=O)—OR'$_1$ group wherein m$_3$ is equal to 1, 2, 3 or 4, or (iii) an alkyl group comprising 1 to 12 carbon atoms.

* * * * *